(12) United States Patent
Lien

(10) Patent No.: US 9,951,076 B2
(45) Date of Patent: Apr. 24, 2018

(54) DEUTERATED PENTYLENETETRAZOLES FOR IMPROVING COGNITIVE FUNCTION

(71) Applicant: Balance Therapeutics, Inc., San Bruno, CA (US)

(72) Inventor: Lyndon Lien, Hillsborough, CA (US)

(73) Assignee: Balance Therapeutics, Inc., Hillsborough, CA (US)

( * ) Notice: Subject to any disclaimer, the term of this patent is extended or adjusted under 35 U.S.C. 154(b) by 0 days.

(21) Appl. No.: 15/246,347

(22) Filed: Aug. 24, 2016

(65) Prior Publication Data

US 2017/0044165 A1 Feb. 16, 2017

Related U.S. Application Data

(63) Continuation of application No. 14/115,307, filed as application No. PCT/US2012/036217 on May 3, 2012, now Pat. No. 9,453,020.

(60) Provisional application No. 61/482,533, filed on May 4, 2011.

(51) Int. Cl.
C07D 487/04 (2006.01)
C07B 59/00 (2006.01)

(52) U.S. Cl.
CPC .......... *C07D 487/04* (2013.01); *C07B 59/002* (2013.01); *C07B 2200/05* (2013.01)

(58) Field of Classification Search
CPC .............................. A61K 31/55; C07D 487/04
USPC ...................... 514/214.02; 540/579
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan | |
| 6,603,008 B1 | 8/2003 | Ando | |
| 7,517,990 B2 | 4/2009 | Ito | |
| 8,729,067 B2 | 5/2014 | Garner et al. | |
| 8,946,206 B2 | 2/2015 | Garner et al. | |
| 2007/0082929 A1 | 4/2007 | Gant | |
| 2007/0197695 A1 | 8/2007 | Potyen | |
| 2008/0009475 A1* | 1/2008 | Garner ................... | A61K 31/34 514/214.02 |

FOREIGN PATENT DOCUMENTS

| | | |
|---|---|---|
| WO | WO 2007139818 | 12/2007 |
| WO | WO 2012151343 | 8/2012 |

OTHER PUBLICATIONS

Browne, Journal of Clinical Pharmacology, 38:213-220 (1998).

Database Registry [Online] Chemical Abstracts Service, Columbus, Ohio, US; Sep. 7, 2011 (Sep. 7, 2011), XP002681631, Database accession No. 1329509-68-3.
Diler et al., "Sex differences in modulating blood brain barrier permeability by NO in pentylenetetrazol-induced epileptic seizures," (Mar. 1, 2007), vol. 80, No. 14, pp. 1274-1281, Life Sciences, Pergamon Press, Oxford, GB.
D'Itri, F.M., et al., "Synthesis of Some Dihalotetrazolopyridines, Asepines, and Azocines," Journal of Heterocylic Chemistry, (Jan. 1, 1970), vol. 7, pp. 221-222.
Dyck et al., Journal of Neurochemistry, 46(2):399-404 (1986).
Fernandez, et al., "Pharmacotherapy for cognitive impairment in a mouse model of Down syndrome," Nature Neuroscience, (2007), vol. 10, No. 4, pp. 411-413.
Foster, A.B., "Deuterium isotope effects in the metabolism of drugs and xenobiotics: implications for drug design," Advances in Drug Research, (Jan. 1, 2985), vol. 13, pp. 1-40, Academic Press, London, GB.
Hackam et al., JAMA, 296(14):1731-1732 (2006).
International Searching Authority, "International Search Report for PCT/US2012/036217," (dated Oct. 11, 2012).
International Searching Authority, "Written Opinion for PCT/US2012/036217," (dated Oct. 11, 2012).
Jordan, Nature Reviews: Drug Discovery, 2:205 (2003).
Kirk et al., "Fluorine in medicinal chemistry: Recent therapeutic applications of fluorinated small molecules," (Aug. 1, 2006), vol. 127, No. 8, pp. 1013-1029., Journal of Fluorine Chemistry, Elsevier, NL.
Kushner et al., Canadian Journal of Physiology and Pharmacology, 77(2):79-88 (1999).
Pieniaszek et al., Journal of Clinical Pharmacology, 39:817-825 (1999).
Rueda, et al., "Chronic pentylenetetrazole but not donepezil treatment rescues spatial cognition in Ts65Dn mice, a model for Down syndrome," Neuroscience Letters, (2008), vol. 433, No. 1, pp. 22-27.

(Continued)

*Primary Examiner* — Douglas M Willis
(74) *Attorney, Agent, or Firm* — Jones Day

(57) ABSTRACT

Provided are compounds having formula I:

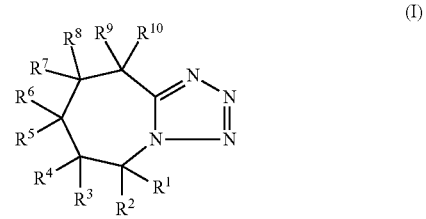

wherein $R^1$, $R^2$, $R^3$, $R^4$, $R^5$, $R^6$, $R^7$, $R^8$, $R^9$, and $R^{10}$ are as disclosed herein, or a pharmaceutically salt thereof. Pharmaceutical compositions comprising the compounds and methods of their use, for instance in treating senility, senile confusion, psychoses, psychoneuroses when anxiety and nervous tension were present, cerebral arteriosclerosis, nausea, depression, fatigue, debilitation, mild behavioral disorders, irritability, emotional instability, antisocial attitudes, anxiety, vertigo or incontinence, or symptom thereof, or in improving cognitive function in individuals, for instance, in individuals with Down syndrome and other conditions, are also provided.

7 Claims, 3 Drawing Sheets

(56) References Cited

OTHER PUBLICATIONS

Squires, R.F., et al., "Convulsant potencies of tetrazoles are highly correlated with actions on GABA/benzodiazepine/picrotoxin receptor complexes in brain," Life Sciences, (Oct. 1984), vol. 35, No. 14, pp. 1439-1444, Pergamon Press, Oxford, GB, XP023720048, ISSN: 0024-3205, (Retrieved on Oct. 1, 1984).
Tonn et al., Biological Mass Spectometry, 22(11):633-642 (1993).
Tung, The Development of Deuerium-Containing Drugs, Innovations in Pharmaceutical Technolgy, Mar. 2010, issue No. 32, pp. 24-28.
Vohland, H. W. et al., "Metabolism of pentetrazole in the rat. Isolation and identification of the main metabolites from urine," Chemical Abstract Service, (1975), pp. 1274-1280, XP002681632, retrieved from STN, Database accession No. 1975:92876.
Wolen, Journal of Clinical Pharmacology, 26:419-424 (1986).

\* cited by examiner

DEUTERATED PENTYLENETETRAZOLES FOR IMPROVING COGNITIVE FUNCTION

CROSS-REFERENCE TO RELATED APPLICATIONS

This application is a continuation of application Ser. No. 14/115,307, filed Apr. 8, 2014, which is the National Stage of International Application No. PCT/US2012/036217, filed May 3, 2012, which claims the benefit of priority to U.S. provisional application No. 61/482,533, filed on May 4, 2011, the content of which is incorporated herein by reference in its entirety.

FIELD

Isotopically-enriched and/or fluorinated pentylenetetrazole (PTZ) compounds and pharmaceutically acceptable salts thereof are provided. Also provided are pharmaceutical compositions and unit dose forms comprising the compounds, methods of using the compounds for the treatment of certain diseases, and methods for the improvement of cognitive impairment in an individual, for instance, in an individual with Down Syndrome.

BACKGROUND

Since being reported as a possible treatment for schizophrenia in the late 1930s, pentylenetetrazole (PTZ) has been used as a therapy for a variety of maladies and conditions involving the central nervous system, such as senile confusion, depression, vertigo, and so forth, as well as being used as a circulatory and respiratory stimulant and cough suppressant. PTZ has the following formula:

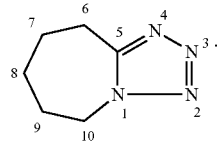

PTZ is known by tradenames and synonyms including METRAZOL, CARDIAZOL pentetrazol, among others. In 1982 the U.S. Food and Drug Administration withdrew its approval for marketing of PTZ in the United States and required that evidence be provided for efficacy in support of claims made for PTZ used alone or in combination with other agents. See 47 *Federal Register* 19208 (May 4, 1982).

PTZ is believed to block or reduce passage of ions through the ion channel associated with type A gamma-aminobutyric acid ($GABA_A$) receptors. GABA is the major inhibitory neurotransmitter in the central nervous system. GABA, in the absence of PTZ and other channel blockers, $GABA_A$ receptor antagonists and/or allosteric modulators, binds to the $GABA_A$ receptor leading to receptor channel opening and passage of chloride ions through the channel.

Recent work has shown that administration of PTZ can lead to improvement in learning and memory. For example, in a transgenic mouse model of Down syndrome, daily doses of PTZ generated improvements in learning lasting months after mice were last exposed to PTZ. See, e.g., Fernandez et al., 2007 *Nature Neuroscience* 10(4):411-413; Rueda et al., 2008, *Neuroscience Letters* 433(1):22-27; and U.S. Patent Application Publication. No. 2008/0009475, published Jan. 10, 2008, which disclosures are incorporated herein by reference in their entireties for all purposes.

Peak concentration of PTZ in blood generally occurs within 10 minutes after intravenous (IV) or intraperitoneal (IP) delivery. PTZ has high bioavailability after oral dosing (PO), and peak blood levels generally occur within approximately 30 to 60 minutes when PTZ is given orally. PTZ readily crosses the blood brain barrier. It has a relatively short plasma half-life of about 60 minutes. Following administration to mice, rats, dogs, humans and other living systems, PTZ undergoes oxidative metabolism, a key determinant for PTZ's short half-life. There are a number of metabolites that have been characterized for PTZ, at least 2 of these are oxidized variants of PTZ and account for over 60% of the eliminated product. These metabolites are 6-hydroxypentetrazole and 8-hydroxypentetrazole. Oxidation is likely carried out by enzymes of the cytochrome P450 superfamily.

Increasing dosing frequency or dosage amounts of PTZ in therapeutic applications to compensate for its relatively short half-life in vivo requires careful consideration in view that its side effects, including seizures and convulsions, are $C_{max}$ driven. PTZ may also cause dose-dependent, significant inhibitory effects on the activity of metabolic enzymes including CYP450 and other members of this superfamily, which could potentially be detrimental when, for instance, PTZ is co-administered with other drugs.

New therapies having a therapeutic benefit similar or improved to that of PTZ are sought. Included in such sought-after therapies would be, for instance, compounds exhibiting a half-life in vivo longer than that for PTZ.

BRIEF SUMMARY

In certain embodiments, provided herein is a compound having Formula I:

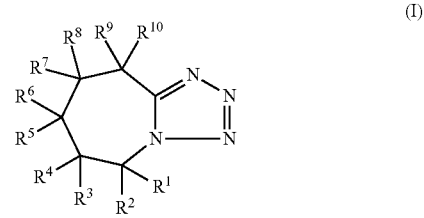

or a pharmaceutically acceptable salt thereof, wherein:
each of $R^1$, $R^2$, $R^3$, $R^4$, $R^5$, $R^6$, $R^7$, $R^8$, $R^9$, and $R^{10}$ is independently selected from hydrogen, deuterium and fluorine, wherein at least one of $R^1$, $R^2$, $R^3$, $R^4$, $R^5$, $R^6$, $R^7$, $R^8$, $R^9$, and $R^{10}$ is not hydrogen.

In certain embodiments, wherein when each of $R^1$, $R^2$, $R^9$, and $R^{10}$ is hydrogen, at least one of $R^3$, $R^4$, $R^5$, $R^6$, $R^7$, and $R^8$ is other than deuterium.

In certain embodiments of the compound of Formula I provided herein, $R^1$, $R^2$, $R^3$, $R^4$, $R^5$, $R^6$, $R^7$, $R^8$, $R^9$, and $R^{10}$ are each independently selected from hydrogen and deuterium.

In some embodiments, the compound having Formula I is selected from the group consisting of compounds 1-8, as provided herein. In some embodiments, the compound having Formula I is selected from group consisting of compounds 1, 2, and 4.

In other embodiments of the compound of Formula I provided herein, $R^1$, $R^2$, $R^3$, $R^4$, $R^5$, $R^6$, $R^7$, $R^8$, $R^9$, and $R^{10}$ are each independently selected from hydrogen and fluorine.

In certain embodiments, the compound having Formula I is selected from the group consisting of compounds 9-13, as provided herein.

In some embodiments, the compound having Formula I is

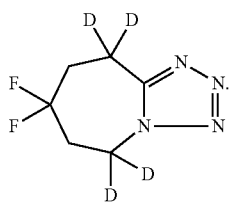

(14)

In some embodiments, provided herein is a pharmaceutical composition comprising a compound having Formula I and a pharmaceutically acceptable excipient.

In other embodiments, a unit dose form comprising 0.1 mg to 1 g of the compound having Formula I and one or more pharmaceutically acceptable excipients is provided. In certain embodiments, the unit dose form is suitable for oral administration to a human.

In yet other embodiments, methods comprising administration an amount of the compound having Formula I are provided. In certain embodiments, the method is provided for increasing blood flow, heart rate, or breathing rate in an individual in need thereof, comprising administering an amount of a compound as described herein to the individual effective to increase blood flow, heart rate, or breathing rate. In some embodiments, the method is for suppressing cough in an individual. In yet other embodiments, provided is a method of treating senility, senile confusion, psychoses, psychoneuroses when anxiety and nervous tension are present, cerebral arteriosclerosis, nausea, depression, fatigue, debilitation, a mild behavioral disorder, irritability, emotional instability, antisocial attitude, anxiety, vertigo, incontinence, or symptom thereof, comprising administering a compound as described herein to an individual with senility, senile confusion, psychoses, psychoneuroses when anxiety and nervous tension are present, cerebral arteriosclerosis, nausea, depression, fatigue, debilitation, mild behavioral disorder, irritability, emotional instability, antisocial attitude, anxiety, vertigo or incontinence, effective to treat senility, senile confusion, psychoses, psychoneuroses when anxiety and nervous tension are present, cerebral arteriosclerosis, nausea, depression, fatigue, debilitation, mild behavioral disorder, irritability, emotional instability, antisocial attitude, anxiety, vertigo, incontinence, or symptom thereof.

In certain embodiments, a method is provided for improving cognitive function in an individual with Down syndrome, phenylketonuria, neurofibromatosis type 1, maple syrup urine disease, Rett syndrome, fetal alcohol syndrome, an autism spectrum disorder, circadian rhythm disruption, Alzheimer's disease, or dementia, the method comprising administering an amount of a compound as described herein to the individual effective to improve cognitive function.

In other embodiments, provided herein is a compound having Formula I for use as a circulatory or respiratory stimulant, or as a cough suppressant. In some embodiments, the compound as described herein is for use in treating senility, senile confusion, psychoses, psychoneuroses when anxiety and nervous tension are present, cerebral arteriosclerosis, nausea, depression, fatigue, debilitation, mild behavioral disorder, irritability, emotional instability, antisocial attitude, anxiety, vertigo or incontinence, or a symptom thereof. In certain embodiments, the compound as described herein is for use in improving cognitive function in an individual with Down syndrome, phenylketonuria, neurofibromatosis type 1, maple syrup urine disease, Rett syndrome, fetal alcohol syndrome, an autism spectrum disorder, circadian rhythm disruption, Alzheimer's disease, or dementia.

DETAILED DESCRIPTION

Figure 1:
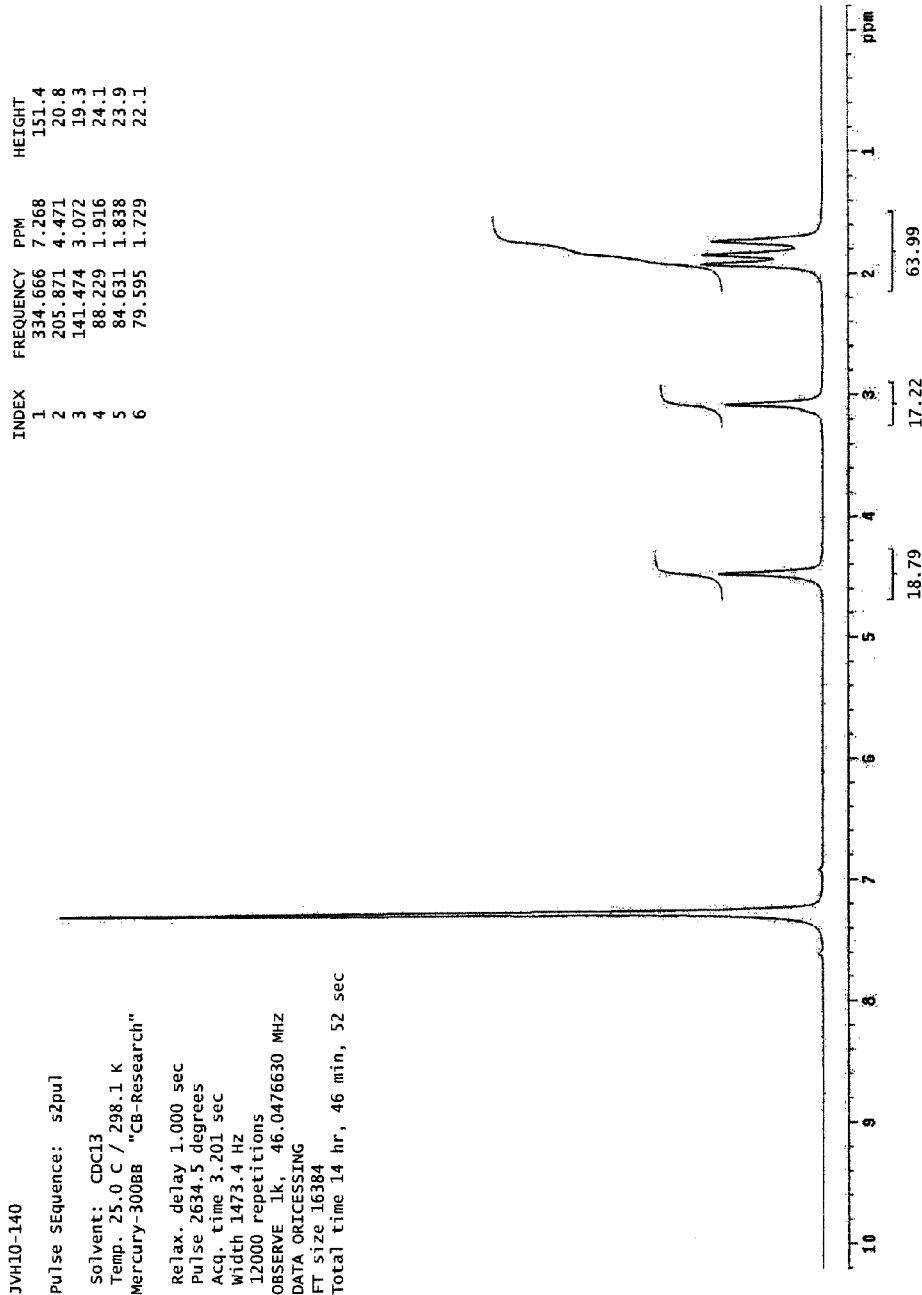
FIG. 1 provides a $^2$H NMR spectrum used in analysis of exemplary compound 1 as described in Example 1 below.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Unless otherwise stated, when a position is designated as "H" or "hydrogen," or when a position in a chemical structure provided herein is implicitly occupied by a hydrogen atom, the position will be understood to have hydrogen at its natural isotopic composition.

Also unless otherwise stated, when a position is designated specifically as "D" or "deuterium", the position is understood to have deuterium at an abundance that is at least 3,340 times greater than the natural abundance of deuterium, which is 0.015% (i.e., at least 50.1% incorporation of deuterium).

The term "deuterium substitution" as used herein refers to the substitution of one or more hydrogen atoms in a molecule with deuterium atoms.

The terms "isotopically enriched" or "isotopical enrichment" as used herein refer to an atom having an isotopic composition other than the natural isotopic composition of that atom or to a compound containing at least one atom having an isotopic composition other than the natural isotopic composition of that atom. For example, in a compound as provided herein, when a position is designated as having deuterium, it will be understood that the abundance of deuterium at that position is substantially greater than the natural abundance of deuterium, which is about 0.015%. "Isotopic enrichment" can be expressed in terms of the percentage of incorporation of an amount of a specific isotope at a given atom in a molecule in the place of the atom's natural isotopic abundance. For example, deuterium enrichment of 1% at a given position means that 1% of molecules in a given sample contain deuterium at the specified position. The "isotopic enrichment" of the compounds provided herein can be determined using conventional analytical methods known to one of ordinary skill in the art, including mass spectrometry and nuclear magnetic resonance spectroscopy.

The term "isotopic enrichment factor" as used herein means the ratio between the isotopic abundance and the natural abundance of a specified isotope within a molecule.

The term "isotopologue" as used herein refers to a species of a specific compound that differs from another species of the given compound only in its isotopic composition, or level of isotopic enrichment, at one or more positions, e.g., H vs. D.

The term "pharmaceutical composition" refers to a composition that is formulated for pharmaceutical use.

The term "pharmaceutically acceptable" as used herein refers to a component that is compatible with other ingredients of a pharmaceutical composition and is suitable for use in contact with tissues of a subject without undue toxicity, irritation, allergic response, immunogenicity or other complications, commensurate with a reasonable benefit/risk ratio.

As used herein, a "pharmaceutically acceptable salt" means any non-toxic salt that, upon administration to a recipient, is capable of providing, either directly or indirectly, a compound of this disclosure. A salt is formed between a basic group of a compound and an acid, or between an acidic group of a compound and a base.

Acids commonly employed to form pharmaceutically acceptable salts include but are not limited to inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, and acetic acid.

Bases commonly employed to form pharmaceutically acceptable salts include but are not limited to inorganic bases such as magnesium hydroxide, calcium hydroxide, potassium hydroxide, zinc hydroxide, and sodium hydroxide, as well as organic bases such as primary, secondary, tertiary, and quaternary, aliphatic and aromatic amines, including but not limited to L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

A pharmaceutically acceptable salt thus includes but is not limited to a sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, and mandelate.

The term "therapeutically effective amount," as used herein refers to a dosage sufficient to produce a desired result, where the desired result is generally (i) an amelioration or alleviation, if not complete cessation, of one or more symptoms of disease or condition being treated, particularly the cognitive impairment symptoms, e.g., memory, learning ability, and the like, or (ii) a measurable improvement in cognitive function as determined on an appropriate assessment test testing some aspect relating to cognition. The term also refers to an amount of a compound that is sufficient to elicit the biological or medical response of a cell, tissue, system, animal, or human that is being sought by a researcher, veterinarian, medical doctor, or clinician.

As used herein, the term "solvate" means a compound that further includes a stoichiometric or non-stoichiometric amount of solvent such as water, acetone, ethanol, methanol, dichloromethane, 2-propanol, or the like, bound by non-covalent intermolecular forces. The term "hydrate" is employed when the solvent is water. Pharmaceutically acceptable solvates and hydrates are complexes of a compound with one or more solvent or water molecules, or 1 to about 100, or 1 to about 10, or 1 to about 2, 3, or 4 solvent or water molecules.

The term "prodrug" as used herein refers to a compound that is a readily converted in vivo into a compound of Formula I as provided herein ("parent compound"). Prodrugs may have advantages over parent compounds, such as, for example, having better bioavailability or greater solubility in pharmaceutical compositions. A prodrug may be converted into the parent drug by various mechanisms, including enzymatic processes and metabolic hydrolysis.

The term "stable compounds," as used herein, refers to compounds which possess stability sufficient to allow for their manufacture, and that maintain the integrity of the compounds for a sufficient period of time to be useful for the purposes detailed herein (e.g., formulation into a pharmaceutical composition, intermediates for use in production of therapeutic compounds, isolatable or storable intermediate compounds, treating a disease or condition responsive to therapeutic agents).

A "subject" as used herein means an animal, preferably a mammal, including, for example, mouse, rat, rabbit, dog, cat, guinea pig, goat, cow, horse, pig, sheep, monkey, primate, ape, or human. The term "individual" as used herein is when the subject is a human.

The term "disorder" as used herein refers to any abnormal condition of the human or animal body or of its parts that impairs normal functioning. A disorder is typically manifested by distinguishing signs and symptoms.

As used herein, "treat," "treating" or "treatment" refer to at least an amelioration of the symptoms associated with the disease or condition afflicting the subject, where amelioration is used in a broad sense to refer to at least a reduction in the magnitude of a parameter, e.g., symptom, associated with the disease or condition being treated, such as impairment in memory or learning ability or mental confusion or depression or other cognitive function. As such, treatment also includes situations where the disease or condition, or at least symptoms associated therewith, are completely inhibited, e.g., prevented from happening, or stopped, e.g., terminated, such that the subject no longer suffers from the disease or condition, or at least the symptoms that characterize the disease or condition. It will be understood that where "treat," "treating" or "treatment" in used in context of treating cognitive impairment, the terms refer to improvement in cognition, for example, as can be determined on an appropriate assessment test.

The term "cognitive impairment" as used herein refers to impairment, often but not always from early childhood, of at least one cognitive function, such as a impairment in memory, impairment in learning ability, etc.

The term "dosing regimen" as used herein refers to a specified amount of compound administered per time unit and duration of dosing (e.g., 3 times/day for 7 days).

The term "about" as used herein is intended to qualify the numerical values that the term modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ ... to $n_2$" or "$n_1$-$n_2$" is used, where $n_1$ and $n_2$ are numbers, then unless otherwise specified, this notation is intended to include the numbers themselves and the range between them. This range may be integral or continuous between and including the end values.

Compounds

PTZ derivatives with increased metabolic stability can, in certain embodiments, provide therapeutic benefits over PTZ, for instance, by (a) enhancing subject compliance by decreasing the number of doses needed to achieve the therapeutic effect of PTZ, (b) decreasing the amount of a dose needed to achieve the therapeutic effect of PTZ and/or reduce the occurrence of potential adverse events, (c) creating a more effective drug and/or a safer drug for polypharmacy, whether the polypharmacy be intentional or not, and/or (d) attenuating inter-patient variability due to polymorphisms in enzymes that normally metabolize PTZ. Compounds that have one or all of these characteristics compared to PTZ are desirable, and are provided herein.

In one aspect, provided herein is a compound having Formula I:

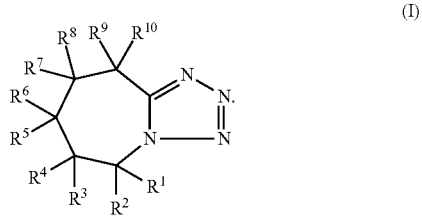

(I)

In Formula I, each of $R^1$, $R^2$, $R^3$, $R^4$, $R^5$, $R^6$, $R^7$, $R^8$, $R^9$, and $R^{10}$ is independently selected from hydrogen, deuterium, and fluorine, wherein at least one of $R^1$, $R^2$, $R^3$, $R^4$, $R^5$, $R^6$, $R^7$, $R^8$, $R^9$, and $R^{10}$ is not hydrogen.

In certain embodiments, compounds of Formula I are provided wherein when each of $R^1$, $R^2$, $R^9$, and $R^{10}$ is hydrogen, at least one of $R^3$, $R^4$, $R^5$, $R^6$, $R^7$, and Re is not deuterium.

In certain embodiments of the compound of Formula I provided herein, $R^1$, $R^2$, $R^3$, $R^4$, $R^5$, $R^6$, $R^7$, $R^8$, $R^9$, and $R^{10}$ are each independently selected from hydrogen and deuterium.

In some embodiments, $R^5$ and $R^6$ are each deuterium. $R^1$, $R^2$, $R^3$, $R^4$, $R^7$, $R^8$, $R^9$, and $R^{10}$ are independently selected from hydrogen and deuterium, or $R^1$, $R^2$, $R^3$, $R^4$, $R^7$, $R^8$, $R^9$, and $R^{10}$ are each hydrogen.

In some embodiments, $R^9$ and $R^{10}$ are each deuterium. $R^1$, $R^2$, $R^3$, $R^4$, $R^5$, $R^6$, $R^7$, and Re are independently selected from hydrogen and deuterium, or $R^1$, $R^2$, $R^3$, $R^4$, $R^5$, $R^6$, $R^7$, and Re are each hydrogen.

In some embodiments, $R^5$, $R^6$, $R^9$, and $R^{10}$ are each deuterium. $R^1$, $R^2$, $R^3$, $R^4$, $R^7$, and Re are independently selected from hydrogen and deuterium, or $R^1$, $R^2$, $R^3$, $R^4$, $R^7$, and Re are each hydrogen.

In some embodiments, $R^1$, $R^2$, $R^5$, $R^6$, $R^9$, and $R^{10}$ are each deuterium. $R^3$, $R^4$, $R^7$, and Re are independently selected from hydrogen and deuterium, or $R^3$, $R^4$, $R^7$, and Re are each hydrogen.

In some embodiments, $R^1$, $R^2$, $R^3$, $R^4$, $R^5$, $R^6$, $R^7$, Re, $R^9$, and $R^{10}$ are each deuterium.

In certain embodiments, provided herein are compounds having the structure of PTZ in which one or more hydrogen are replaced with a deuterium or fluorine. In certain embodiments, a deuterium isotopologue of PTZ is provided.

Deuterium (referred to as "D" in certain formulas herein) is a stable, non-radioactive isotope of hydrogen. One characteristic of deuterium is that it forms particularly strong bonds with carbon, generally about six to ten times more stable than the corresponding hydrogen to carbon bond. General exposure to and incorporation of deuterium is safe within levels potentially achieved by use of compounds provided herein as therapeutics.

It will be recognized that some variation of natural isotopic abundance occurs in a synthesized compound depending upon the origin of chemical materials used in the synthesis. Thus, typically, any preparation of a compound, e.g., PTZ, will inherently contain small amounts of deuterium isotopologues. The concentration of naturally abundant stable hydrogen isotopes, notwithstanding this variation, is small and immaterial as compared to the degree of stable isotopic substitution of compounds provided herein.

A deuterium isotopologue of PTZ as provided herein, can, for example, have a minimum isotopic enrichment factor of at least 3,000 (a deuterium enrichment of 45%) for each designated deuterium in the isotopologue. In other embodiments, a deuterium isotopologue of PTZ as provided herein has an isotopic enrichment factor for each designated deuterium of at least 3,500 (52.5% deuterium enrichment), at least 4,000 (60% deuterium enrichment), at least 4,500 (67.5% deuterium enrichment), at least 5,000 (75% deuterium enrichment), at least 5,500 (82.5% deuterium enrichment), at least 6,000 (90% deuterium enrichment), at least 6,333.3 (95% deuterium enrichment), at least 6,466.7 (97% deuterium enrichment), at least 6,600 (99% deuterium enrichment), or at least 6,633.3 (99.5% deuterium enrichment).

The relative amount of deuterium in the deuterium isotopologues of PTZ provided herein will depend upon a number of factors including the isotopic purity of deuterated reagents used to make the compound and the efficiency of incorporation of deuterium in the various synthesis steps used to prepare the compound. In certain embodiments, for a given deuterium isotopologue of PTZ provided herein, the relative amount of other isotopologues will be less than 49.9% of the isotopologues in toto. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5%.

In some embodiments, a compound of Formula I provided herein is selected from the group consisting of the following compounds:

(1)
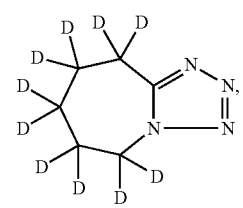

(2)
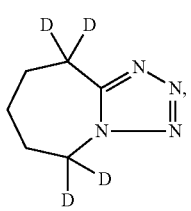

(3)
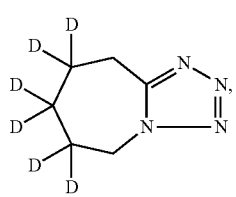

(4)
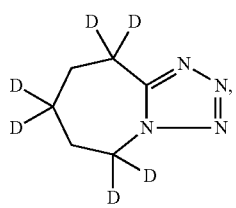

(5)
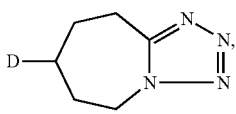

(6)
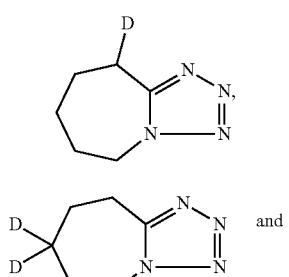

(7)
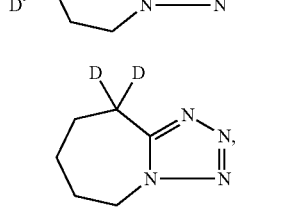

and (8)

or a pharmaceutically acceptable salt thereof.

In certain embodiments, the compound of Formula I is selected from the group consisting of the following compounds:

(1)
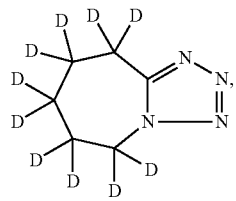

(2)
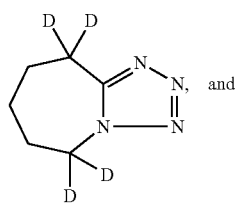

and (4)
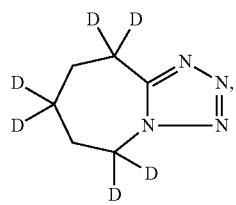

or pharmaceutically acceptable salt thereof.

In certain embodiments, the compound of Formula I is selected from the group consisting of the following compounds, or a pharmaceutically acceptable salt thereof:

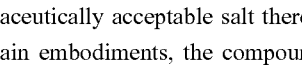

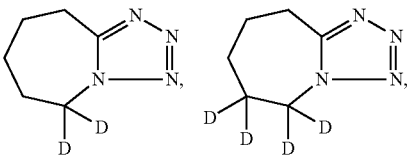

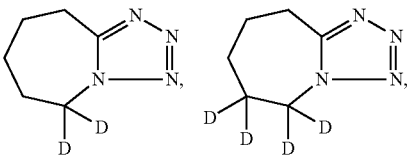

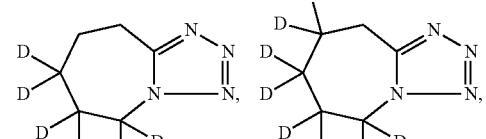

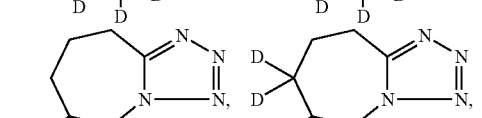

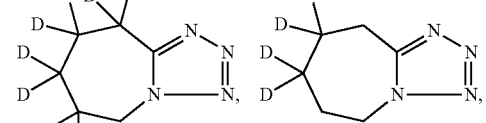

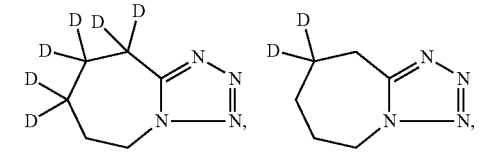

-continued

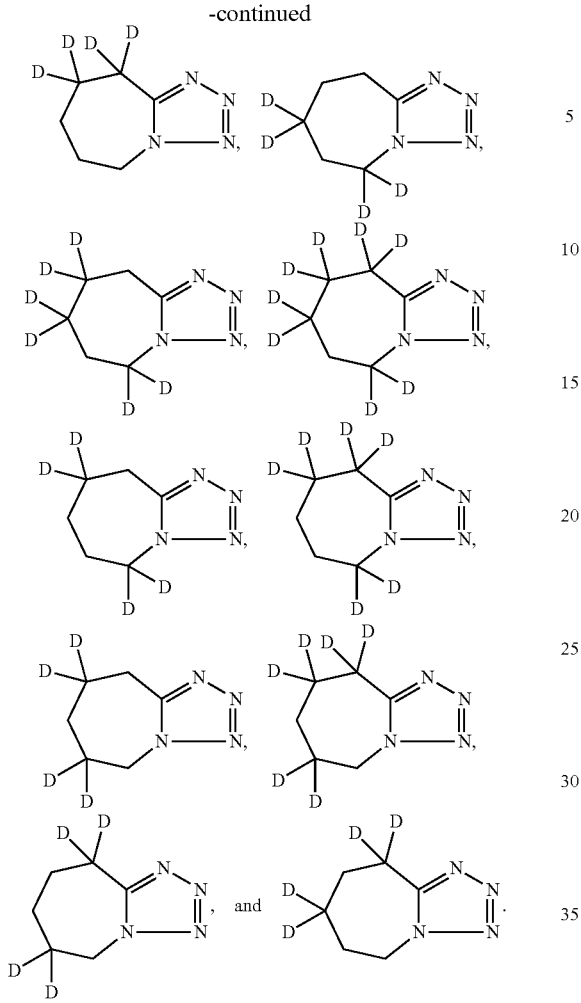

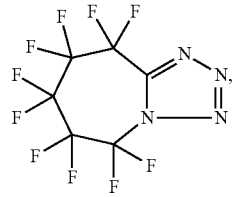

(9)

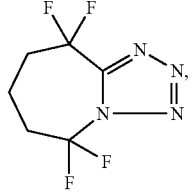

(10)

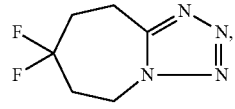

(11)

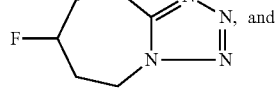

(12) and

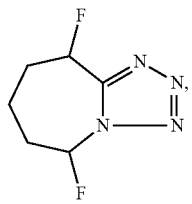

(13)

or a pharmaceutically acceptable salt thereof.

In certain embodiments, a compound is provided selected from the group consisting of:

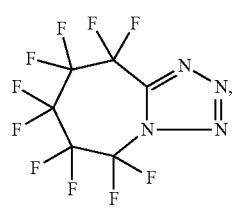

(9)

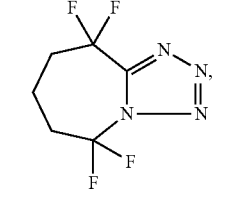

(10)

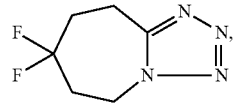

(11)

In other embodiments of the compound of Formula I provided herein, each of $R^1$, $R^2$, $R^3$, $R^4$, $R^5$, $R^6$, $R^7$, $R^8$, $R^9$, and $R^{10}$ is independently selected from hydrogen and fluorine.

In some embodiments, $R^5$ and $R^6$ are each fluorine. $R^1$, $R^2$, $R^3$, $R^4$, $R^7$, $R^8$, $R^9$, and $R^{10}$ are independently selected from hydrogen and fluorine, or $R^1$, $R^2$, $R^3$, $R^4$, $R^7$, $R^8$, $R^9$, and $R^{10}$ are each hydrogen.

In some embodiments, $R^9$ and $R^{10}$ are each fluorine. $R^1$, $R^2$, $R^3$, $R^4$, $R^5$, $R^6$, $R^7$, and $R^8$ are independently selected from hydrogen and fluorine, or $R^1$, $R^2$, $R^3$, $R^4$, $R^5$, $R^6$, $R^7$, and $R^8$ are each hydrogen.

In some embodiments, $R^5$, $R^6$, $R^9$, and $R^{10}$ are each fluorine. $R^1$, $R^2$, $R^3$, $R^4$, $R^7$, and $R^8$ are independently selected from hydrogen and fluorine, or $R^1$, $R^2$, $R^3$, $R^4$, $R^7$, and $R^8$ each hydrogen.

In some embodiments, $R^1$, $R^2$, $R^5$, $R^6$, $R^9$, and $R^{10}$ are each fluorine. $R^3$, $R^4$, $R^7$, and $R^8$ are independently selected from hydrogen and fluorine, or $R^3$, $R^4$, $R^7$, and $R^8$ are each hydrogen.

In some embodiments, $R^1$, $R^2$, $R^3$, $R^4$, $R^5$, $R^6$, $R^7$, $R^8$, $R^9$, and $R^{10}$ are each fluorine.

In some embodiments, each of $R^1$, $R^2$, $R^9$, and $R^{10}$ is deuterium and each of $R^5$ and $R^6$ is fluorine.

In certain embodiments, a compound is provided selected from the group consisting of:

-continued

(12) 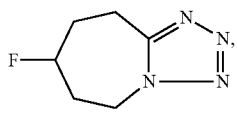

(13) 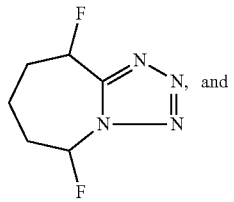

(14) 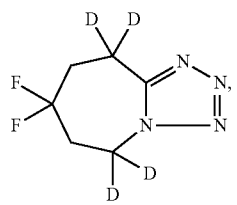

or a pharmaceutically acceptable salt thereof.

In certain embodiments, the compound of Formula I is selected from the group consisting of the following compounds, or a pharmaceutically acceptable salt thereof:

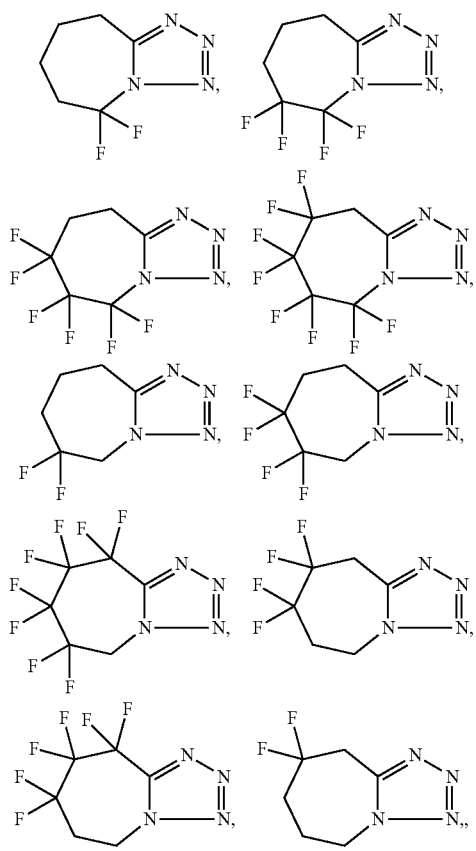

-continued

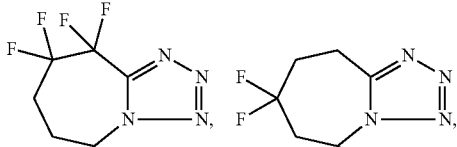

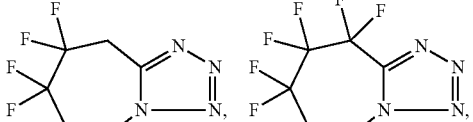

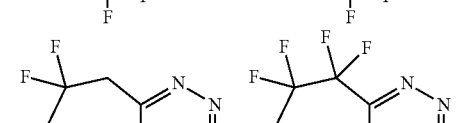

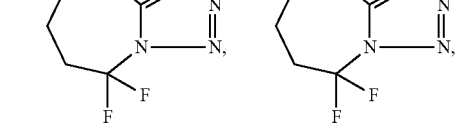

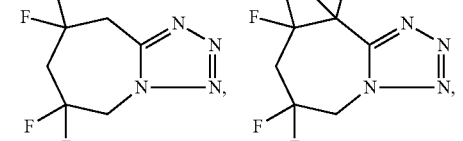

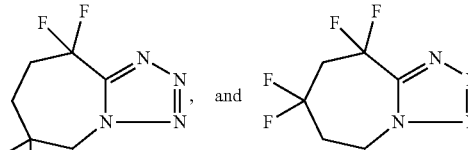

Without intending to be bound by any particular theory or mechanism, in certain embodiments, it is believed that one or more compounds of Formula I provided herein can, when administered to a population of individuals, exhibit decreased inter-individual variation in plasma levels as compared to the inter-individual variation in plasma levels of non-deuterated, non-fluorinated PTZ when administered to a population of individuals in an equivalent dosage unit. In certain embodiments, it is believed that one or more compounds of Formula I provided herein will, when administered to a population of individuals, exhibit average plasma levels greater than the average plasma level of non-deuterated, non-fluorinated PTZ when administered in an equivalent dosage unit to a population of individuals. In yet other embodiments, it is believed that one or more compounds of Formula I provided herein will, when administered to a population of individuals, exhibit peak plasma concentration s lower than the peak plasma concentration of non-deuterated, non-fluorinated PTZ when administered in an equivalent dosage unit to a population of individuals.

In certain embodiments, the term "compound," unless otherwise indicated in the context in which it is used, encompasses its pharmaceutically acceptable salts, solvates (including hydrates), and/or prodrugs.

Synthesis

Compounds of Formula I provided herein may be prepared by reference to the known methods for making PTZ.

Such methods can be carried out utilizing corresponding deuterated and/or fluorinated and optionally, other isotope-containing reagents and/or intermediates to synthesize the compounds provided herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography). For instance, certain intermediates or reagents useful for making PTZ may be replaced with corresponding deuterated or fluorinated intermediates or reagents as may be needed depending on the desired site or sites or deuterium or fluorine incorporation, as exemplified below.

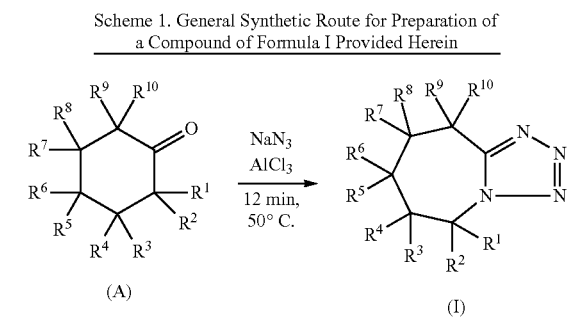

Scheme 1 shows a general synthetic route useful for preparing compounds of Formula I provided herein, including, for example, exemplary compounds 1, 2, 3, 4, 5, 6, 7, 8, 9, 10, 11, 12 and 13 (as provided above), as well as other deuterated and/or fluorinated versions of PTZ. In this scheme, each R is independently selected from H, D, or F, with the proviso that at least one R is D or F.

Alternatively deuterated and/or fluorinated versions of PTZ can be prepared from the appropriately substituted ε-caprolactam following the procedure described by Lehnhoff and Ugi, 1995, *Heterocycles*, 40(2): 801-808.

For instance, commercially available substituted cyclohexanones useful as reagent A for the synthesis of compounds of Formula I provided herein, for example, compounds 1, 2, 3, 9, 10, 11 and 12 according to Scheme 1 are, respectively, the following cyclohexanones:

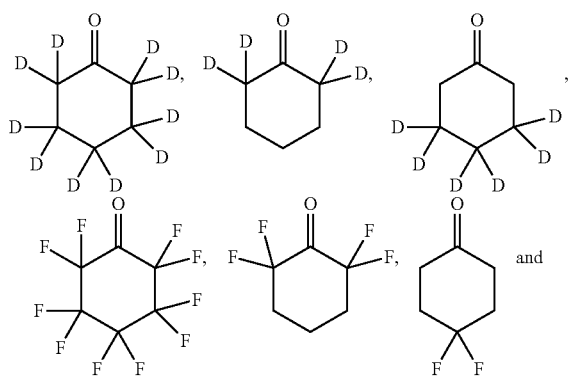

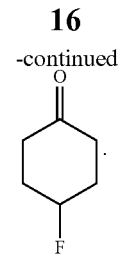

An exemplary synthesis of a reagent A useful for the preparation of compound 4 is described in Lompa-Krzymien and Leitch, 1973, *Journal of Labelled Compounds and Radiopharmaceuticals*, 9(2): 331-338. An exemplary synthesis of a reagent A useful for the preparation of compound 5 is described in Williams et al., 1964, *Monatshefte fuer Chemie*, 95(1): 166-177. An exemplary synthesis of a reagent A useful for the preparation of compound 6 is described in Takei et al., 2003, *Journal of Organometallic Chemistry*, 679(1): 32-42. An exemplary synthesis of a reagent A useful for the preparation of compound 7 is described in Wehage and Heesing, 1992, *Chem. Ber.*, 125(1): 209-215. An exemplary synthesis of a reagent A useful for the preparation of compound 8 is described in Deutsch and Mandelbaum, 1969, *Tetrahedron Letters*, 10(17): 1351-2. An exemplary synthesis of a reagent A for the preparation of compound 13 is described in Cantacuzene and Atlani, 1970, *Tetrahedron*, 26(10): 2447-2468.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formula I provided herein and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Commercial sources for deuterium isotopically enriched starting materials or reagents include, among others, Icon Services Inc. (Summit, N.J. USA), Cambridge Isotope Laboratories (Andover, Mass. USA) and Sigma-Aldrich Corp. (St. Louis, Mo. USA). Methods of incorporating deuterium in target compounds are extensively documented. See, for instance, *Journal of Labelled Compounds and Radiopharmaceuticals* (John Wiley & Sons Ltd.), for numerous issues that provided detailed experimental descriptions on incorporation of deuterium into bioactive organic molecules.

Pharmaceutical Compositions and Unit Dose Forms

In one aspect, provided herein is a pharmaceutical composition comprising a compound of Formula I provided herein or a pharmaceutically acceptable salt, solvate, or prodrug thereof (collectively referred to below as "the active ingredient") and a pharmaceutically acceptable excipient.

A pharmaceutical composition, as provided herein, is formulated to be compatible with its intended route of administration. Examples of routes of administration include, but are not limited to, parenteral, e.g., intravenous, intradermal, subcutaneous, intramuscular, oral and transdermal (topical) administration. In a specific embodiment, the composition is formulated in accordance with routine procedures as a pharmaceutical composition adapted for intravenous, subcutaneous, intramuscular, oral or topical administration to subjects. In some embodiments, a pharmaceutical composition is formulated in accordance with routine procedures for oral administration to humans. Typically, compositions for intravenous administration are solutions in sterile isotonic aqueous buffer. Where necessary, the composition may also include a solubilizing agent and a local anesthetic such as lidocaine to ease pain at the site of the injection.

Excipients are inert substances such as, without limitation, carriers, diluents, fillers, coloring agents, flavoring agents, sweeteners, lubricants, solubilizers, suspending agents, binders, vehicles, wetting agents, tablet disintegrating agents and encapsulating material. The choice of excipient, to a large extent, depends on factors, such as the particular mode of administration, the effect of the excipient on the solubility and stability of the active ingredient, and the nature of the dosage form.

For example, pharmaceutically acceptable excipients, including carriers, adjuvants, vehicles, and the like, that may be used in the pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In making the pharmaceutical compositions, the active ingredient may be mixed with a diluent, or enclosed within a carrier, which may be in the form of a capsule, sachet, paper, or other container. Consistent with its intended route of administration, the pharmaceutical compositions can be in a solid, semi-solid, or liquid form, for example, in the form of tablets, enteric coated tablets, soft or hard gelatin capsules, depots, pills, powders, lozenges, elixirs, suspensions, emulsions, slurrys, solutions, sterile injectable solutions, sterile packaged powders, suppositories, suspensions, syrups, aerosols, ointments, and the like. In certain embodiments, the pharmaceutical compositions contain, for example, up to 0.5%, up to 1%, up to 10%, or up to 25% or more by weight of the active ingredient. Pharmaceutical compositions provided herein may be formulated according to conventional pharmaceutical practice (see, e.g., *Remington: The Science and Practice of Pharmacy, 21st edition*, A. R. Gennaro, ed. (Lippincott Williams & Wilkins, Phildelphia Pa., 2005) and *Encyclopedia of Pharmaceutical Technology, Third Edition*, J. Swarbrick, editor (Informa Healthcare USA, Inc., New York, 2006)).

In certain embodiments, the pharmaceutical composition is suitable for oral, parenteral, or intravenous infusion administration.

Oral administration can include, for instance, buccal, lingual or sublingual administration.

In some embodiments, the pharmaceutical composition is in the form of a tablet or a capsule suitable for oral administration.

Tablets, for instance, can further comprise a sweetening agent, a flavoring agent, a coloring agent, a preservative, or some combination of these in order to provide pharmaceutically elegant and palatable preparation In certain embodiments, the pharmaceutical composition is pyrogen-free.

Pharmaceutical compositions may be presented in unit dose forms containing a predetermined amount of active ingredient per unit dose, suitable for administration to a subject. In some embodiments, a unit dose form is provided comprising a compound of the present disclosure and one or more pharmaceutically acceptable excipients. Unit dose forms, as used herein, refer to physically discrete units suitable for administration to human and animal subjects and packaged individually as is known in the art. Each unit dose contains a predetermined quantity of the active ingredient(s) sufficient to produce the desired therapeutic effect, in association with the pharmaceutical excipients. Examples of unit dose forms include ampoules, syringes, and individually packaged tablets and capsules. Unit dose forms may be administered in fractions or multiples thereof.

The pharmaceutical composition, including unit dose form, can be in a form such as, for example, a single tablet, pill, capsule, a single solution for intravenous injection, a single drinkable solution, a single patch, and the like. Routes of administration of the unit dose forms include those described above.

The unit dose form can, for example, comprise 0.1 mg to 1 gram of the active ingredient. In certain embodiments, the unit dose form comprises 0.1 mg to 50 mg, 0.5 mg to 200 mg, 1 mg to 100 mg, 10 mg to 250 mg, 50 mg to 500 mg, or 100 mg to 1 g of the active ingredient. In certain embodiments, the unit dose form comprises an amount of the active ingredient consistent with the doses described below for administration to a subject in a method as provided herein.

In certain embodiments, the unit dose form comprises 0.1 mg to 1 g or 0.5 mg to 200 mg of the active ingredient and one or more pharmaceutically acceptable excipients, wherein the unit dose form is suitable for oral administration to a human.

In other embodiments, the pharmaceutical composition or unit dose form is in the form of a controlled or delayed release formulation. The present invention also provides new formulations and unit dose forms useful in the methods provided below, including controlled or delayed release and sustained release formulations useful in these methods. In these methods, the effective dose is as described above, but the dose is only administered once per day, as the sustained release or controlled or delayed release formulation achieves the same therapeutic benefit as more frequent dosing of an immediate-release formulation. Technology for controlled or delayed release and sustained release formulations, including those formulated into beads, coated tablets including osmotically-controlled release tablets are known in the art, for example, as described in U.S. Pat. Nos. 3,062,720; 3,247,066; 4,256,108; 4,160,452; and 4,265,874. In some embodiments, oral compositions can be made, using known technology, which specifically release orally-administered agents in the small or large intestines of a human patient, as described in, for example, Hardy et al., 1987, *Alimentary Pharmacology & Therapeutics* 1(4) 273-280 or U.S. Pat. No. 4,663,308. Other controlled or delayed release or sustained released formulations may be employed, for instance as described in International Publication No. WO 01/12233, U.S. Pat. Nos. 3,773,919 and 4,767,628, and U.S. Patent Application Publication No. 20030068384. Such formulations can be used in implants that release an agent over a period of several hours, a day, a few days, a few weeks or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and. US20020019446.

In certain embodiments, a sustained release or controlled or delayed release formulation of the active ingredient is delivered during the day, evening or night so that a minimum therapeutic concentration of the active ingredient in the brain is maintained for a period of time generally greater than 2 or generally greater than 3, generally greater than 4, generally greater than 6, generally greater than 8, or generally greater than 12 hours.

In other embodiments, a pulsatile release formulation of the active ingredient is delivered so that 2, 3 or 4 pulses of the active ingredient are delivered over a 12 hour cycle. The effective total dose is as described above; the pulsatile release formulation is administered once per day, as the release profile and the mode of release obviates the need for multiple daily dosing.

Pulsed release technology such as that described in U.S. Pat. Nos. 4,777,049 and 6,555,136 can thus be used to administer the active agent to a specific location within the gastrointestinal tract. Such systems permit drug delivery at a predetermined time and can be used to deliver the active agent, optionally together with other additives that may alter the local microenvironment to promote agent stability and uptake, directly to the colon, without relying on external conditions other than the presence of water to provide in vivo release.

Methods

In one aspect, provided herein are methods comprising administering a compound of the present disclosure, to a subject to (i) stimulate systemic blood circulation and/or respiration in the subject; (ii) suppress coughing in the subject; (iii) treat a disease or condition that the subject has, where the disease or condition is selected from the group consisting of senility, senile confusion, psychoses, psychoneuroses when anxiety and nervous tension are present, cerebral arteriosclerosis, nausea, depression, fatigue, debilitation, mild behavioral disorder, irritability, cognitive impairment, emotional instability, antisocial attitude, anxiety, vertigo and incontinence; or (iv) improve cognition in the subject.

In embodiments of methods for improving cognition, the subject can, for example, have a cognitive impairment. In certain embodiments, the cognitive impairment is due to a congenital disorder. Exemplary congenital disorders where cognitive impairment can be present include Down syndrome, phenylketonuria, neurofibromatosis type 1, maple syrup urine disease, Rett syndrome, and fetal alcohol syndrome.

In some embodiments, the cognitive disorder can have a genetic and/or environmental cause. For instance, in certain embodiments, the method for improving cognition comprises administering a compound of the present disclosure to a subject with an autism spectrum disorder.

In yet other embodiments of the methods for improving cognition, the subject can have a cognitive impairment due to, for example, an acquired condition. For example, cognitive impairment can be from circadian rhythm disruption or a neurodegenerative condition, including Alzheimer's disease and other forms of dementia.

Congenital, acquired and neurodegenerative forms of cognitive impairment reduce the capacity for individuals to store and retrieve memories, learn, communicate and function independently.

In certain embodiments, provided herein are methods of improving cognition in a subject with intellectual disability (mental retardation). By intellectual disability is meant a cognitive impairment with a pattern of persistently slow learning of basic motor and language skills during childhood, and a significantly below-normal global intellectual capacity as an adult. One common criterion for diagnosis of intellectual disability is a tested IQ of 70 or below.

Conditions of interest for treatment, including conditions for improving cognitive function, include Down Syndrome, and other congenital or acquired conditions that impair cognitive function. Included in the conditions of interest for treatment are those in which there is impairment, often from early childhood, of at least one cognitive function, such as a impairment in memory, impairment in learning ability, etc. Down syndrome is the most common form of intellectual disability with an incidence rate of about 1 in 700 births and a prevalence of more than 400,000 in the U.S. and just under 6 million worldwide. It is a genetic condition also called Trisomy 21 in which persons with Down syndrome have 3 copies of chromosome 21 rather than 2. Cognitive impairment in Down syndrome is characterized by IQs that range generally from 35 to 70, mental age equivalents of about 7 years of age, and pronounced deficits in memory and language.

In certain situations, methods provided herein may result in partial or in a complete removal of a deficit in the cognitive function. For instance, the amount of improvement can be at least about 2 fold, at least about 5 fold or at least about 10 fold as compared to a suitable control, e.g., an otherwise substantially identical subject not administered a compound as provided herein, that is, a subject having similar a level of cognitive ability that has been administered a placebo, where in certain embodiments the amount of improvement is at least about 1.5 fold, about 2 fold, about 3 fold, about 5 fold, about 10 fold, about 15 fold, about 20 fold, about 25 fold, about 50 fold, about 75 fold, about 100 fold or greater. In certain embodiments, an improvement in cognitive function can be at least about 1% or greater. In some embodiments the improvement can be about 1%, about 2%, about 3%, about 4%, about 5%, about 6%, about 7%, about 8%, about 9%, about 10%, about 12%, about 15%, about 20%, about 25%, about 30%, about 40%, about 50%, about 60%, about 70%, about 80% or greater.

In some embodiments, the improvement is determined by measuring some aspect of cognitive function in a given subject (or population of subjects) before and after administration of a PTZ derivative that is a compound as provided herein. In some embodiments, the aspect of cognitive function can be measured in a given subject (or population of subjects) prior to being administered a PTZ derivative as provided herein, which measurement is then compared to a measurement of the aspect of cognitive function during or upon completion of a dosing regimen lasting a period of time (e.g., administrations made over a period of days, weeks, months or even years). In some embodiments, the improvement is determined by measuring some aspect of cognitive function in a population of subjects to whom are administered (at least once, or, in other embodiments, a dosing regimen) of a PTZ derivative as provided herein as compared to measurements made in a population of subjects to whom the PTZ derivative as provided herein is not administered.

Assessing treatment efficacy or improvement in cognitive function can be evaluated using any test or protocol known in the art. For instance, the Clinician's Global Impression of Change (CGI/C) has been one of the most commonly used test to assess overall change in clinical trials. The validity of this type of measure is based on the ability of an experienced clinician to detect clinically relevant against trivial change in a patient's overall clinical state.

Assessing "improvement in cognitive function" can, for example, include a clinical history and/or collection of standardized information. Assessment may include, for instance, intelligence quotient (IQ) testing. It will be understood that an improvement in cognitive function can refer to any measurable improvement in an aspect of cognition, for example, as determined by performance of a task intended to assess recognition, comprehension, reasoning, remembering, creation of imagery, conation, capacity for judgment, learning, etc., or aspect thereof. The cognitive function improvement can be evaluated using any convenient protocol. A variety of assessment tests are known in the art. See, e.g., Borkowski et al., "Intellectual Assessment and Intellectual Disability" in *Handbook of Intellectual and Developmental Disabilities* (eds. Jacobson et al., Springer Science+Business Media, LLC, New York, 2007), Chapter 14, pages 261-278.

Assessment tests include, for example, the Diagnostic Adaptive Behavior Scale (DABS); the Wechsler Adult Intelligence Scale (WAIS) including it revisions, WAIS-R and WAIS-III; the Mini-Mental State Examination (MMSE) or "Folstein" test; the Blessed Information-Memory-Concentration Test (BIMC); Fuld Object Memory Evaluation (FOME); the California Verbal Learning Test (CVLT) and revised version (CVLT-II); and the like.

The compound provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations. In particular, compounds as provided herein may cause epileptic activity and doses should be well below a dose that will kindle seizures. Orally administered PTZ has, in humans, a kindling dose of approximately 20 mg/kg.

Advantageously, the deuterium or fluorine containing analogue of PTZ provided herein may be may be suitable for administration in smaller doses, or may be suitable for fewer multiple administrations, to a subject than that for PTZ for a given indication.

Doses of the compounds administered in the methods provided in this disclosure can, for example, be in the range of from 0.005 mg/kg to 10 mg/kg, from 0.001 mg/kg to 0.2 mg/kg, from 0.01 to mg/kg to 2 mg/kg, or from 0.05 to mg/kg to 0.5 mg/kg, where "kg" refers to the subject's body mass. In certain embodiments, an administered dose is about 10 mg/kg of patient weight, about 5 mg/kg, about 3 mg/kg, about 1 mg/kg, about 0.3 mg/kg, about 0.1 mg/kg, about 0.05 mg/kg, about 0.025 mg/kg, or about 0.01 mg/kg. An effective dose can be in the range of, for example, from 0.01 mg to 1.25 gm per dose, from 1 mg to 250 mg per dose, or from 2.5 mg to 70 mg per dose. The daily dose can be in the range of, for example, 0.1 mg to 5 gm per day, or from 1 mg to 1 gram per day, or from 3 mg to 300 mg per day. In various embodiments, the administered dose is about 1 gm, about 500 mg, about 250 mg, about 200 mg, about 100 mg, about 50 mg, about 25 mg, about 10 mg, about 5 mg, about 1 mg, about 0.5 mg, about 0.25 mg, or about 0.05 mg, which may be administered once, twice, three times or four time per day. In certain embodiments, the dose administered is that as provided above for the unit dose forms.

The dosage regimen with the use of the compounds provided herein is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds provided herein may be administered in a single daily dose, or the total daily dose may be administered in divided doses, two, three, or more times per day. Where delivery is via transdermal forms, administration is continuous.

In accordance with the methods provided, the compounds provided herein can, for example, be administered in a dosing regimen. A dosing regimen can, for example, comprise administering a compound as provided herein to a subject once a day for several days, weeks, months or years. A dosing regimen is usually maintained for at least about two days, at least about one week, at least about two weeks, at least about three weeks, at least about one month, or longer. In some embodiments of the invention, an intermittent dosing regimen is used, i.e., once a month, every other week, every other day, once per week, twice per week, and the like.

In one aspect provided herein are methods for blocking ion flow through the ion channel associated with the $GABA_A$ receptor in a cell. Such methods comprise the step of contacting the cell with a compound or pharmaceutical composition provided herein.

In one aspect provided herein are methods for inhibiting GABA activation of receptors in the CNS of a subject. Such methods comprise the step of administering to the subject a compound or pharmaceutical composition provided herein.

In one aspect provided herein are methods for treating a subject suffering from, or being susceptible to suffering from, a disorder that is beneficially treated by PTZ. Such methods comprise the step of administering to the subject a therapeutically effective amount of a compound or pharmaceutical composition provided herein.

In one aspect, provided herein are methods of treating a subject suffering from, or being susceptible to suffering from, a disorder that is beneficially treated by PTZ wherein the methods comprise the step of administering to the subject a therapeutically effective amount of a compound or pharmaceutical composition provided herein so as to effect: (1) decreased inter-individual variation in plasma levels of the compound or a metabolite thereof; (2) increased average plasma levels of the compound or decreased average plasma levels of at least one metabolite of the compound per dosage unit; (3) decreased metabolism by at least one cytochrome P450 or monoamine oxidase isoform in the subject; (4) decreased metabolism via at least one polymorphically-expressed cytochrome P450 isoform in the subject; (5) at least one improved sign or symptom of the disorder, in each case of (1)-(5), as compared to PTZ. In certain embodiments, inter-individual variation in plasma levels of the compound or metabolites thereof is decreased; average plasma levels of the compound are increased; average plasma levels of a metabolite of the compound are decreased; inhibition of a cytochrome P450 or monoamine oxidase isoform by the compound is increased; or metabolism of the compound by at least one polymorphically-expressed cytochrome P450 isoform is decreased; by greater than about 5%, greater than about 10%, greater than about 20%, greater than about 30%, greater than about 40%, or by greater than about 50% as compared to PTZ.

In one aspect, provided herein are methods for treating a subject suffering from, or being susceptible to suffering from, cognitive impairment wherein the method comprises the step of administering to the subject a derivative of PTZ (a compound as provided herein) that upon administration provides a greater plasma exposure level of the derivative of PTZ than the plasma exposure level of a molar equivalent of PTZ administered in the same dosing regimen and to an equivalent subject. In certain embodiments, the plasma exposure level is at least 110%, at least 115%, at least 120%, at least 125%, at least 130%, at least 135%, at least about 140%, at least about 145%, or more of the plasma exposure level of PTZ. In some embodiments, the derivative of PTZ has a longer plasma half-live than PTZ as compared to a molar equivalent PTZ composition that is administered using the same dosing regimen. In some embodiments, the derivative of PTZ has a decreased rate and amount of metabolite production as compared to a molar equivalent PTZ composition that is administered using the same dosing regimen. In some embodiments, the administration of the derivative of PTZ provides both an increase in the plasma exposure level of the derivative of PTZ and a decrease in the plasma exposure level of metabolites as compared to the plasma exposure level of PTZ and PTZ metabolites produced from a molar equivalent of PTZ administered in the same dosing regimen. Plasma exposure levels of a compound or of metabolites may be measured using the methods described by Li et al., 2005, *Rapid Communications in Mass Spectrometry* 19: 1943-1950; Jindal et al., 1989, *Journal of Chromatography, Biomedical Applications* 493(2): 392-7; Schwartz et al., 1966, *Biochemical Pharmacology* 15(5): 645-55; Mehvar et al., 1987, *Drug Metabolism and Disposition* 15(2): 250-5; Roberts et al., 1981, *Journal of Chromatography, Biomedical Applications* 226(1): 175-82; and any references cited therein or any modifications made thereof.

EXAMPLES

Example 1: Synthesis of $d_{10}$-6,7,8,9-Tetrahydro-5H-tetrazolo[1,5-a]azepine (1)

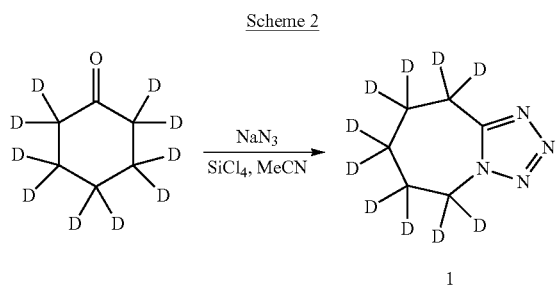

Silicon tetrachloride (0.35 mL, 3 mmol, 1.0 equiv) was added dropwise to a light suspension of $d_{10}$-cyclohexanone (CDN Isotopes, 99.3 atom % D) (0.31 mL, 3 mmol, 1.0 equiv), sodium azide (0.59 g, 9 mmol, 9.0 equiv) and anhydrous acetonitrile (12 mL). The mixture warmed slightly and the suspension became thicker. After the mixture was stirred at room temperature for 15 hr, an aliquot was quenched into 10% sodium carbonate solution and extracted with dichloromethane. TLC showed a barely detectable amount of compound 1 had been formed. After additional 24 hr, TLC of a quenched aliquot showed that greater amount of compound 1 had been formed but higher $R_f$ components remained. The reaction was continued for a total of 6.5 days to maximize the formation of compound 1. The reaction suspension was poured slowly into cold 10% sodium carbonate solution in deuterium oxide (50 mL) and the aqueous mixture extracted with dichloromethane (3×25 mL). The combined dichloromethane layers were washed with saturated brine (10 mL), dried over sodium sulfate, filtered and the filtrate concentrated under reduced pressure to give a pale yellow oil that slowly crystallized. The crude product was re-dissolved in a minimum volume of dichloromethane and absorbed onto silica gel. The absorbed material was purified on an ANALOGIX automated chromatography system eluting with gradient of 25 to 75% ethyl acetate in heptanes to give a solid. The solid was triturated with heptanes, filtered and dried overnight in a vacuum oven at 25-30° C. to give compound 1 (429 mg) as a white solid.

Compound 1 characterization: Melting point: 59.4-59.5° C. Purity: >99% by GC analysis on HP-1 GC capillary column (30 m×320 μm×0.25 μm; hold at 50° C. for 1 min, ramp 20° C./min to 280° C., 1 min hold at 280° C.; retention time=7.51 min). Mass spectrometry, m/z=149.1 (M+H+). $^1$H NMR, $^2$H NMR and $^{13}$C NMR spectra, where each was performed in CDCl$_3$, were consistent with product being compound 1. FIG. 1 provides a representative $^2$H NMR spectrum.

Example 2: Synthesis of 6,6,10,10-d₄-6,7,8,9-Tetrahydro-5H-tetrazolo[1,5-a]azepine (2)

Scheme 3

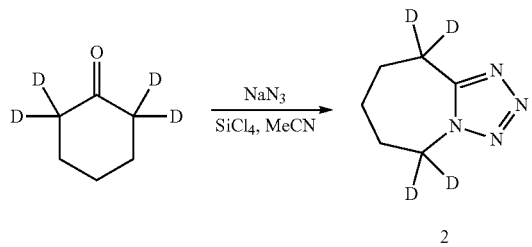

2

Silicon tetra-chloride (0.72 mL, 7.85 mmol, 1.2 equiv) was added dropwise to a suspension of 2,2,6,6-d₄-cyclohexanone (Aldrich Isotopes, 98 atom % D) (0.64 g, 6.26 mmol, 1.0 equiv), sodium azide (1.22 g, 18.76 mmol, 3 equiv) in anhydrous acetonitrile (24 mL). The mixture was stirred at room temperature over the weekend (60 hr). An aliquot was quenched into 10% sodium carbonate solution in D₂O and extracted with EtOAc. TLC indicated compound 2 was generated and a small amount of starting material. The reaction suspension was poured into cold 10% sodium carbonate (36 mL) in deuterium oxide and the aqueous mixture was extracted with ethyl acetate twice (1×150 mL and 1×50 mL). The combined organic layers were dried over sodium sulfate, filtered and concentrated under reduced pressure to give the crude product as a pale yellow oil (0.8 g), which was re-dissolved in a minimum volume of dichloromethane and absorbed onto silica gel (3.4 g). The absorbed material was purified on an ANALOGIX automated chromatography system (SF25-12 g) eluting with a gradient of 20 to 80% ethyl acetate in heptanes to give compound 2 (400 mg, 45% yield) as a white solid which was dried in vacuum oven at 25-30° C.

Compound 2 characterization: Melting point: 59.0-59.1° C. Purity: 99.7% by GC analysis on HP-1 GC capillary column (30 m×320 μm×0.25 μm; split method: 20:1, hold at 50° C. for 1 min, ramp 20° C./min to 280° C., 1 min hold at 280° C.; retention time=7.49 min). Mass spectrometry, m/z=143.1 (M+H⁺). ¹H NMR, ¹³C NMR, COSY NMR and ²H NMR spectra, where each was performed in CDCl₃, were consistent with product being compound 2.

Example 3: Synthesis of 6,6,8,8,10,10-d₆-6,7,8,9-tetrahydro-5H-tetrazolo[1,5-a]-azepine (4)

Scheme 4

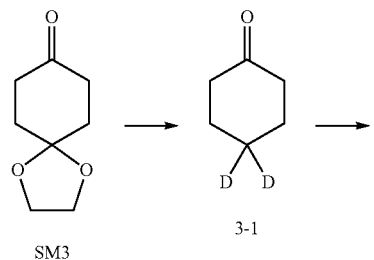

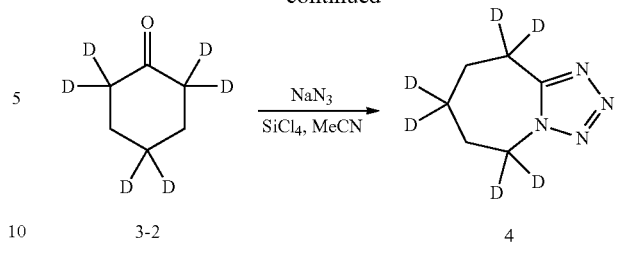

p-Toluenesulfonylhydrazide (6.0 g, 32 mmol, 1 equiv) was added to a solution of 1,4-cyclohexandione monoethyleneketal (SM3) (5.0 g, 32 mmol, 1.0 equiv) in methanol-d (60 mL). The solution became very thick and stirring was continued for 1 hour. Sodium borodeuteride (4 g, 96 mmol, 3 equiv) was added slowly portionwise to the reaction. Note: Be cautious during this addition, and leave large amounts of headspace in the reaction vessel. This reaction starts slowly but eventually evolves large amounts of gas with foaming.

After the addition of sodium borodeuteride was complete, reaction was refluxed for 1 hour. The reaction was cooled to room temperature and 10% hydrochloric acid was added (100 mL). The reaction was stirred for 10 minutes, and extracted with dichloromethane (3×50 mL). The combined organic layers were washed with saturated sodium bicarbonate (5×50 mL). The organic layer was dried over sodium sulfate and the reaction was concentrated to ~30 mL under reduced pressure (low vacuum) at ~30° C. This residue was transferred to a vial and the remaining solvent was removed with a nitrogen stream to give 3-1 as a yellow oil mixed with ~40% p-toluenesulfonyl hydrazide, 3.2 g total mass (~1.3 g product), 40% yield.

4,4-d₂-Cyclohexanone (3-1) (1.6 g crude, 6.5 mmol, 1.0 equiv) was suspended in 10% potassium carbonate in deuterium oxide (20 mL) and acetonitrile (0.5 mL). The reaction was stirred for 36 hours at which time NMR indicated the reaction was complete. The reaction was extracted with dichloromethane (3×10 mL). The combined organic layers were dried over sodium sulfate, filtered and the resulting solution concentrated using a nitrogen stream to give 3-2 as an orange oil (320 mg, 47% yield).

Sodium azide (563 mg, 8.7 mmol, 3 equiv) and silicon tetrachloride (0.375 mL, 3.2 mmol, 1 equiv) was slowly added to a solution of 2,2,4,4,6,6-d₆-cyclohexanone (3-2) (300 mg, 2.9 mmol, 1 equiv) in anhydrous acetonitrile (5 mL). The reaction was stirred at room temperature for ~40 hours, when GC showed complete reaction. The reaction was cooled to 0° C. and 10% sodium carbonate in deuterium oxide (3 mL) was added slowly to the reaction. The reaction was stirred for 30 minutes. The gel-like suspension was filtered through Celite and the Celite was washed with ethyl acetate (10 mL). The layers were separated and the ethyl acetate was dried over sodium sulfate. The reaction was filtered, dried over sodium sulfate and concentrated under reduced pressure to give 180 mg of material that was ~90% pure by GC. This material was chromatographed on ANALOGIX automated column chromatography system eluting with gradient of 0 to 100% ethyl acetate in heptanes to give 3 (80 mg, 27% yield) as a white solid.

Compound 4 characterization: Melting point: 58.1-59.3° C. Purity: 99.8% by GC analysis on HP-1 GC capillary column (see Example 1 for details; retention time=7.52 min). Mass spectrometry, m/z=145.2 (M+H⁺). ¹H NMR, ¹³C NMR, $^2$H NMR and COSY NMR spectra, where each was performed in CDCl$_3$, were consistent with product being compound 4.

Example 4: Synthesis of 7,7-Difluoro-6,7,8,9-tetrahydro-5H-tetrazolo[1,5-a]azepine (11)

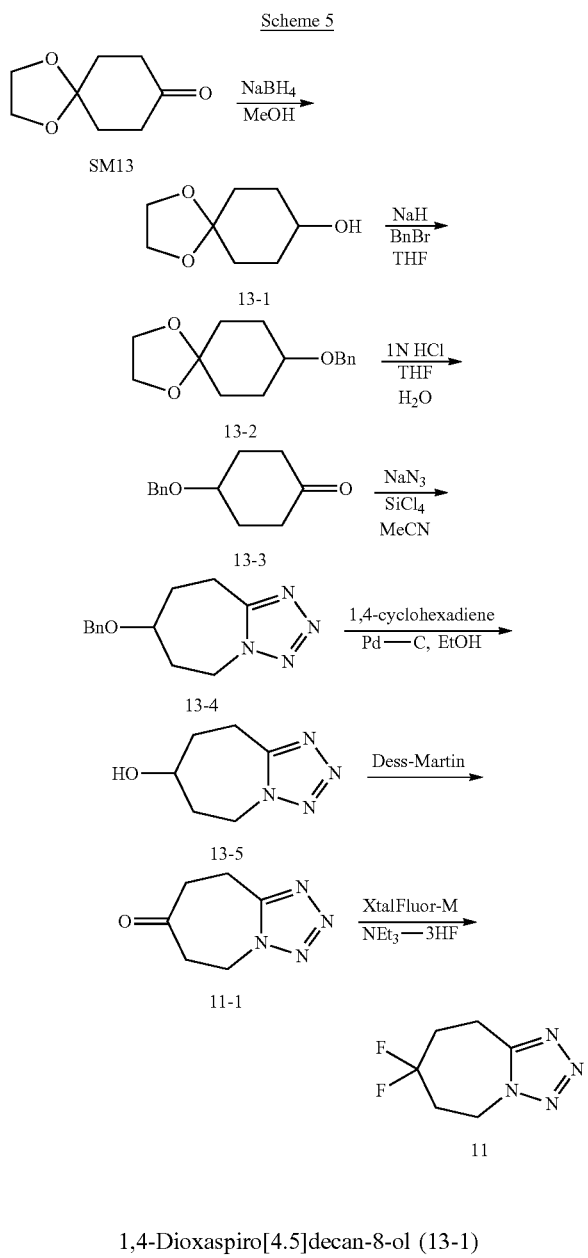

Scheme 5

1,4-Dioxaspiro[4.5]decan-8-ol (13-1)

A cold (0° C.) solution of cyclohexanedione monoethylene ketal (SM13) (6.24 g, 40 mmol, 1.0 equiv) in methanol (90 mL) was treated portionwise with sodium borohydride (1.60 g, 42 mmol, 1.05 equiv). The addition was exothermic and H$_2$ was evolved. The reaction temperature was kept below 10° C. on addition of each portion, allowing the mixture to re-cool to 0° C. before the next addition. When addition of sodium borohydride was complete, the mixture was stirred at 0° C. for 0.75 hours then stirred 1.5 hours while warming to room temperature. The mixture was concentrated under reduced pressure to remove most of the methanol. The residual oily solid was diluted with water (40 mL) and saturated brine (40 mL)—no oil separated. The mixture was saturated with sodium chloride and extracted with ethyl acetate (3×50 mL). The combined organic layers were washed with saturated brine (25 ml), dried over sodium sulfate, filtered and the filtrate concentrated under reduced pressure. The residual colorless oil was redissolved in ethyl acetate (15 mL), the solution diluted with heptanes (45 mL) and the turbid solution concentrated to give crude compound 13-1 (6.17 g) as a colorless oil. Crude compound 13-1 was used subsequently.

8-(Benzyloxy)-1,4-dioxaspiro[4.5]decane (13-2)

A suspension of 60% sodium hydride in mineral oil (1.93 g, 48.3 mmol, 1.25 equiv) in THF (50 mL) was cooled in an ice-water bath. A solution of crude compound 13-1 (6.10 g, 38.6 mmol, 1.0 equiv) in THF (40 mL) was added slowly to maintain at less than 5° C. The mixture was stirred in an ice-water bath for 20 minutes, allowed to warm to room temperature and stirred ihour. Evolution of H$_2$ was very slow. The mixture was warmed to ~45° C. and held for 1 hour (evolution of H$_2$ had essentially ceased). The tan suspension was cooled to room temperature and benzyl bromide (7.26 g, 5.0 mL, 42.5 mmol, 1.1 equiv) was added dropwise. No noticeable exotherm occurred on addition, however, after addition was complete the reaction temperature slowly increased from 21 to 25° C. over 0.25 hours. The mixture was stirred at room temperature over a weekend. The mixture was quenched by the very slow addition of saturated ammonium chloride (45 mL). The biphasic suspension was diluted with water (15 mL) and extracted with a 1 to 1 of ethyl acetate and heptanes (150 mL). The organic phase was washed with saturated brine (2×50 mL), dried sodium sulfate, filtered and the filtrate concentrated under reduced pressure. The residual yellow oil was dissolved in a minimum volume of dichloromethane, absorbed onto silica gel and dry-loaded on a column of silica gel packed in heptanes. The column was eluted with a gradient of 0 to 15% ethyl acetate in heptanes to give 13-2 (9.15 g) as a pale yellow oil.

4-(Benzyloxy)cyclohexanone (13-3)

1N HCl (60 mL) was added to a solution of 13-2 (9.15 g. 36.9 mmol) in THF (90 mL) and the mixture stirred at room temperature for 18 hr. The mixture was concentrated under reduced pressure to remove most of the THF. The residual aqueous oil was made alkaline by slow addition of saturated sodium bicarbonate and extracted with a 1 to 2 mixture of ethyl acetate and heptanes. The organic layer was washed with saturated brine (50 mL), dried over sodium sulfate, filtered and the filtrate concentrated under reduced pressure to give crude 13-3 (7.53 g) as a yellow oil. Crude 13-3 was used subsequently.

7-(Benzyloxy)-6,7,8,9-tetrahydro-5H-tetrazolo[1,5-a]azepine (13-4)

Sodium azide (5.95 g, 91.5 mmol, 3.0 equiv) was added to a solution of crude 13-3 (6.22 g, 20.5 mmol, 1.0 equiv) in acetonitrile (120 mL). Silicon tetrachloride (3.6 mL, 30.5 mmol, 1.0 equiv) was added dropwise to the suspension and the mixture stirred at room temperature with the suspension becoming thicker. After ~20 hours, the thick yellow suspension was poured slowly into cold (~5° C.) 10% sodium carbonate (700 mL). The suspension was extracted with ethyl acetate (3×200 mL, 1×100 mL)—some insolubles remained in the aqueous phase. The combined organic layers were washed with saturated brine (2×150 mL), dried over sodium sulfate, filtered and the filtrate concentrated under reduced pressure to give a tan solid. TLC (50% ethyl acetate in heptanes, Hanessian's stain) showed 13-3, some higher $R_f$ impurities and baseline material. The crude product was dissolved in ethyl acetate (250 mL), silica gel (5 g) and charcoal (0.7 g) were added and the solution stirred at 40° C. for 0.25 hr. The mixture was filtered through a CELITE pad, washing the pad with ethyl acetate (400 mL). The filtrate was concentrated under reduced pressure to give a light tan solid. The crude product was purified on an ANALOGIX automated chromatography system eluting with 0 to 5% methanol in dichloromethane to give 13-4 (4.12 g, ~91% purity by LCMS) as an off-white solid.

6,7,8,9-Tetrahydro-5H-tetrazolo[1,5-a]azepin-7-ol (13-5)

A mixture of 1,4-cyclohexadiene (10.13 g, 11.8 mL, 126.6 mmol, 7.5 equiv), 20% Pd/C (0.41 g, 50% wet), and 13-4 (4.12 g, 16.88 mmol, 1.0 equiv) in ethanol (150 mL) was refluxed for 21.5 hours. The mixture was cooled to room temperature and filtered through a CELITE pad, washing the pad with ethanol (200 mL). The filtrate (slightly turbid) was concentrated to give a grayish-white solid. The solid was dissolved in warm acetone (100 mL), the solution cooled and filtered through a CELITE pad, washing the pad with acetone (100 mL). The filtrate was concentrated to give a solid that was triturated with MTBE (50 mL), filtered and dried for 17 hr in a vacuum oven at 40-45° C. for 17 hours to give 13-5 (2.24 g) as a light gray solid.

8,9-Dihydro-5H-tetrazolo[1,5-a]azepin-7(6H)-one (11-1)

Dess-Martin periodinane (630 mg, 1.52 mmol, 1.3 equiv) was added to a solution of 6,7,8,9-tetrahydro-5H-tetrazolo [1,5-a]azepin-7-ol (13-5) (200 mg, 1.29 mmol, 1.0 equiv) in THF (3.0 mL) The mixture was stirred overnight. Saturated sodium bicarbonate (20 mL) was added to the reaction and stirred for 30 minutes. The mixture was extracted with dichloromethane (3×50 mL). The combined organic layers were dried over sodium sulfate, filtered and concentrated under reduced pressure. The residue was chromatographed on AnaLogix automated column chromatography system eluting with gradient of 30 to 100% ethyl acetate in heptanes to give 11-1 (70 mg, 36% yield) as a white solid.

7,7-Difluoro-6,7,8,9-tetrahydro-5H-tetrazolo[1,5-a] azepine (11)

Triethylamine trihydrofluoride (0.13 mL, 0.8 mmol, 3.0 equiv) and XTALFLUOR-M reagent (126 mg, 0.52 mmol, 2.0 equiv) were sequentially added to a solution of 8,9-dihydro-5H-tetrazolo[1,5-a]azepin-7(6H)-one (11-1) (40 mg, 0.26 mmol, 1.0 equiv) in dichloromethane (3 mL). The mixture was stirred overnight at room temperature. Saturated sodium bicarbonate (10 mL) was added to the reaction and stirred for 30 minutes. The mixture was extracted with dichloromethane (3×50 mL). The combined organic layers were dried over sodium sulfate, filtered and concentrated under reduced pressure The residue was chromatographed on ANALOGIX automated column chromatography system eluting with gradient of 10 to 40% ethyl acetate in heptanes to give 11 (30 mg, 66% yield) as a white solid.

Figure 2:
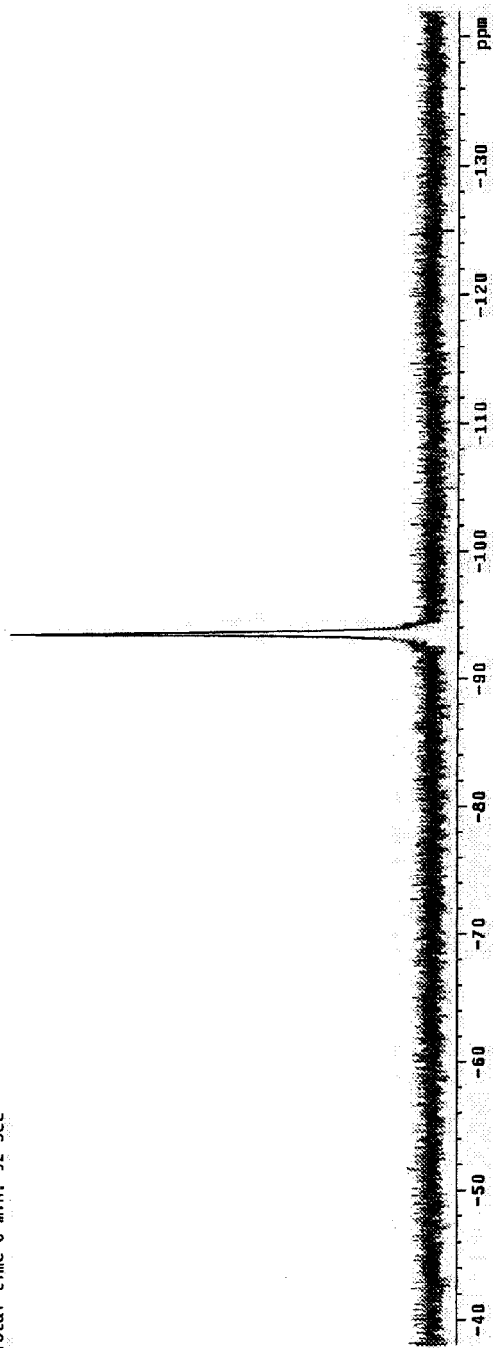
FIG. 2 provides a $^{19}$F NMR spectrum used in analysis of exemplary compound 11 as described in Example 4 below.

Compound 11 characterization: Purity: >99% by GC analysis on HP-5MS GC capillary column (30 m×250 μm×0.25 μm; hold at 50° C. for 1 min, ramp 20° C./min to 280° C., 1 min hold at 280° C.; mobile phase, 5% phenyl methyl siloxane, retention time=7.37 min). GC-MS, m/z=174.0 [M]$^+$. $^1$H NMR, COSY NMR, $^{13}$C NMR, and $^{19}$F NMR spectra, where each was performed in CDCl$_3$, were consistent with product being compound 11. FIG. 2 provides a representative $^{19}$F NMR spectrum.

Example 5: Synthesis of 6,6,10,10-d$_4$-8,8-Difluoro-6,7,8,9-tetrahydro-5H-tetrazolo[1,5-a]azepine (14)

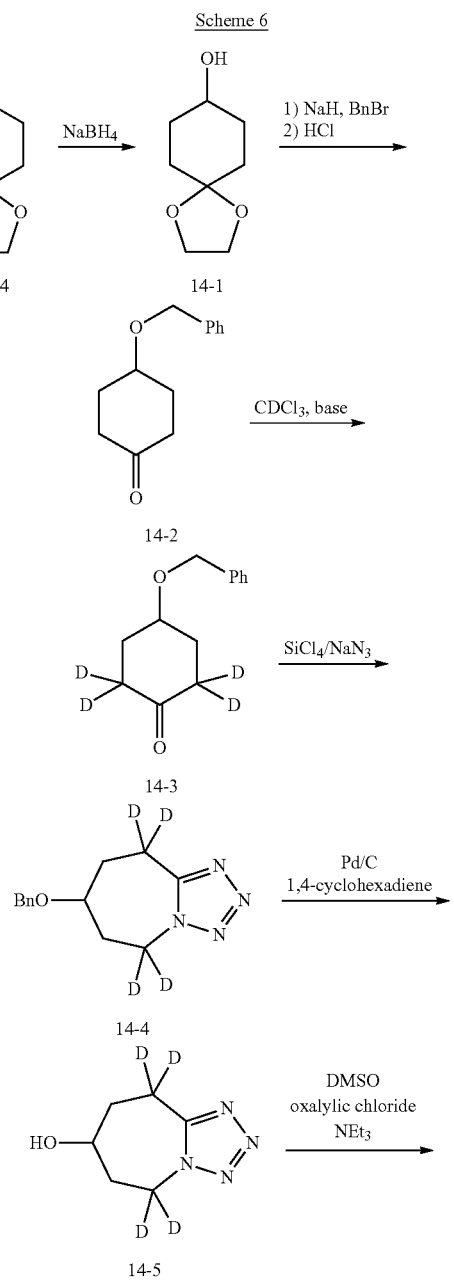

Scheme 6

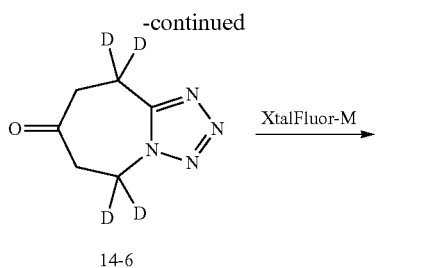

1,4-Dioxaspiro[4.5]decan-8-ol (14-1)

Sodium borohydride (0.8 g, 21 mmol, 1.05 equiv) was added at 0 to 10° C. in portions to a solution of 1,4-dioxaspiro[4.5]decan-8-one (SM14) (3.1 g, 20 mmol, 1.0 equiv) was dissolved in methanol (50 mL). The mixture was stirred at room temperature for 3 h and concentrated under reduced pressure to remove most of solvent. Water (50 mL) was added and the mixture and stirred for 30 minutes. The mixture was extracted with ethyl acetate (3×50 mL) and the combined organic layers were washed with sequentially with 1N HCl (30 mL), water and saturated brine. The organic layer was dried over sodium sulfate, filtered and concentrated under reduced pressure to give 14-1 (3.0 g, 96% yield) as a colorless oil which was used subsequently.

4-(Benzyloxy)cyclohexanone (14-2)

A 60% dispersion of sodium hydride in mineral oil (760 mg, 23 mmol, 1.2 equiv) was added to a solution of 1,4-Dioxaspiro[4.5]decan-8-ol (14-1) (3.0 g, 19 mmol, 1.0 equiv) in anhydrous THF (50 mL) at 0° C. After 6 hours benzyl bromide (2.5 mL, 21.3 mmol, 1.1 equiv) was added to the mixture. The mixture was stirred at room temperature overnight. A 4N HCl solution (30 mL) was added and the reaction was stirred at room temperature for an additional 6 hours. The reaction was neutralized to pH~7 with 4N sodium hydroxide and extracted with ethyl acetate (3×100 mL). The combined organic layers were dried over sodium sulfate, filtered and concentrated under reduced pressure. The residue was purified on an AnaLogix automated column chromatography system eluting with gradient of 0 to 30% ethyl acetate in heptanes to give 14-2 (3.0 g, 77% yield) as a light yellow oil.

4-(Benzyloxy)-2,2,6,6-d$_4$-cyclohexanone (14-3)

Triazabicyclodecene (TBD) (200 mg, 1.44 mmol, 0.1 equiv) was added to a solution of 4-(Benzyloxy)cyclohexanone (14-2) (3.0 g, 14.7 mmol, 1.0 equiv) was dissolved in chloroform-d (50 mL). The mixture was stirred at room temperature overnight, at which point $^1$H-NMR showed 85% deuterium incorporation. The mixture was then refluxed for 6 hours, at which point $^1$H-NMR showed deuterium exchange was complete. The reaction was cooled to room temperature and washed sequentially with 1N HCl (20 mL), water, and saturated brine. The organic layer was dried over sodium sulfate, filtered and concentrated under reduced pressure to give 14-3 (3.0 g, 98% yield) as a light-yellow oil which was used subsequently.

8-(Benzyloxy)-6,6,10,10-d$_4$-6,7,8,9-tetrahydro-5H-tetrazolo[1,5-a]azepine (14-4)

Sodium azide (2.81 g, 43.2 mmol, 3.0 equiv) and silicon tetrachloride (1.65 mL, 14.4 mmol, 1.0 equiv) were added to a solution of 4-(benzyloxy)-2,2,6,6-d$_4$-cyclohexanone (14-3) (3.0 g, 14.4 mmol, 1.0 equiv) in anhydrous acetonitrile (40 mL). The reaction was stirred at room temperature for 48 hours and poured into ice cold saturated sodium bicarbonate (100 mL). The mixture was stirred for 30 minutes and extracted with dichloromethane (3×150 mL). The combined organic layers were dried over sodium sulfate, filtered, and concentrated under reduced pressure. The residue was purified on ANALOGIX automated column chromatography system eluting with a gradient of 0 to 5% methanol in chloromethane to give 14-4 (2.7 g, 75% yield, 7% proton at positions 6 and 10) as white solid.

6,6,10,10-d$_4$-6,7,8,9-Tetrahydro-5H-tetrazolo[1,5-a]azepin-7-ol (14-5)

7-(Benzyloxy)-6,6,10,10-d$_4$-6,7,8,9-tetrahydro-5H-tetrazolo[1,5-a]azepine (14-4) (2.7 g, 10.9 mmol, 1.0 equiv) was dissolved in ethanol (200 mL) followed by the addition of 20% Pd/C (270 mg, 50% wet) and 1,4-cyclohexadiene (12 mL, 127 mmol, 12 equiv). The mixture was refluxed overnight, cooled to room temperature, and filtered through a CELITE pad, washing the pad with ethanol (100 mL). The filtrate was concentrated under reduced pressure to give 14-5 (1.55 g, 90% yield) as an off-white solid which was used subsequently.

6,6,10,10-d$_4$-8,9-Dihydro-5H-tetrazolo[1,5-a]azepin-7(6H)-one (14-6)

Anhydrous DMSO (0.8 mL, 22 mmol, 2.4 equiv) was added to a solution of oxalyl chloride (0.95 mL, 11 mmol, 1.2 equiv) at −78° C. in dichloromethane (20 mL). The mixture was stirred for 0.5 hours at −78° C. followed by the dropwise addition of a solution of 6,6,10,10-d4-6,7,8,9-tetrahydro-5H-tetrazolo[1,5-a]azepin-7-ol (14-5) (1.5 g, 9.5 mmol, 1.0 equiv) in dichloromethane (200 mL) maintaining the temperature below −65° C. The reaction was stirred for an additional 2 hours at −78° C. Triethylamine (7.7 mL, 55 mmol, 6 equiv) was added and the mixture was stirred for 30 minutes at −78° C. After warming to room temperature, water (100 mL) was added and the organic layer was separated, washed with water, saturated brine, dried over sodium sulfate, filtered, and concentrated under reduced pressure. The residue was purified on ANALOGIX automated column chromatography system eluting with eluting with a gradient of 0 to 5% methanol in dichloromethane to give 14-6 (800 mg, 55% yield) as white solid.

6,6,10,10-d$_4$-8,8-Difluoro-6,7,8,9-tetrahydro-5H-tetrazolo[1,5-a]azepine (14)

Triethylamine hydrofluoride (0.68 mL, 4.2 mmol, 3.0 equiv) and XTALFLUOR-M reagent (680 mg, 2.8 mmol, 2.0 equiv) were added sequentially to a solution of 6,6,10, 10-d4-8,9-Dihydro-5H-tetrazolo[1,5-a]azepin-7(6H)-one (14-6) (220 mg, 1.4 mmol, 1.0 equiv) in dichloromethane (10 mL). The mixture was stirred overnight at room temperature followed by the addition of saturated sodium bicarbonate (30 mL). The mixture stirred for 30 minutes and extracted with dichloromethane (3×50 mL). The combined organic layers was dried over sodium sulfate, filtered and concentrated under reduced pressure. The residue was purified on an ANALOGIX automated column chromatography system eluting with gradient of 10 to 40% ethyl acetate in heptanes to give 14 (200 mg, 80% yield) as a white solid.

Figure 3:
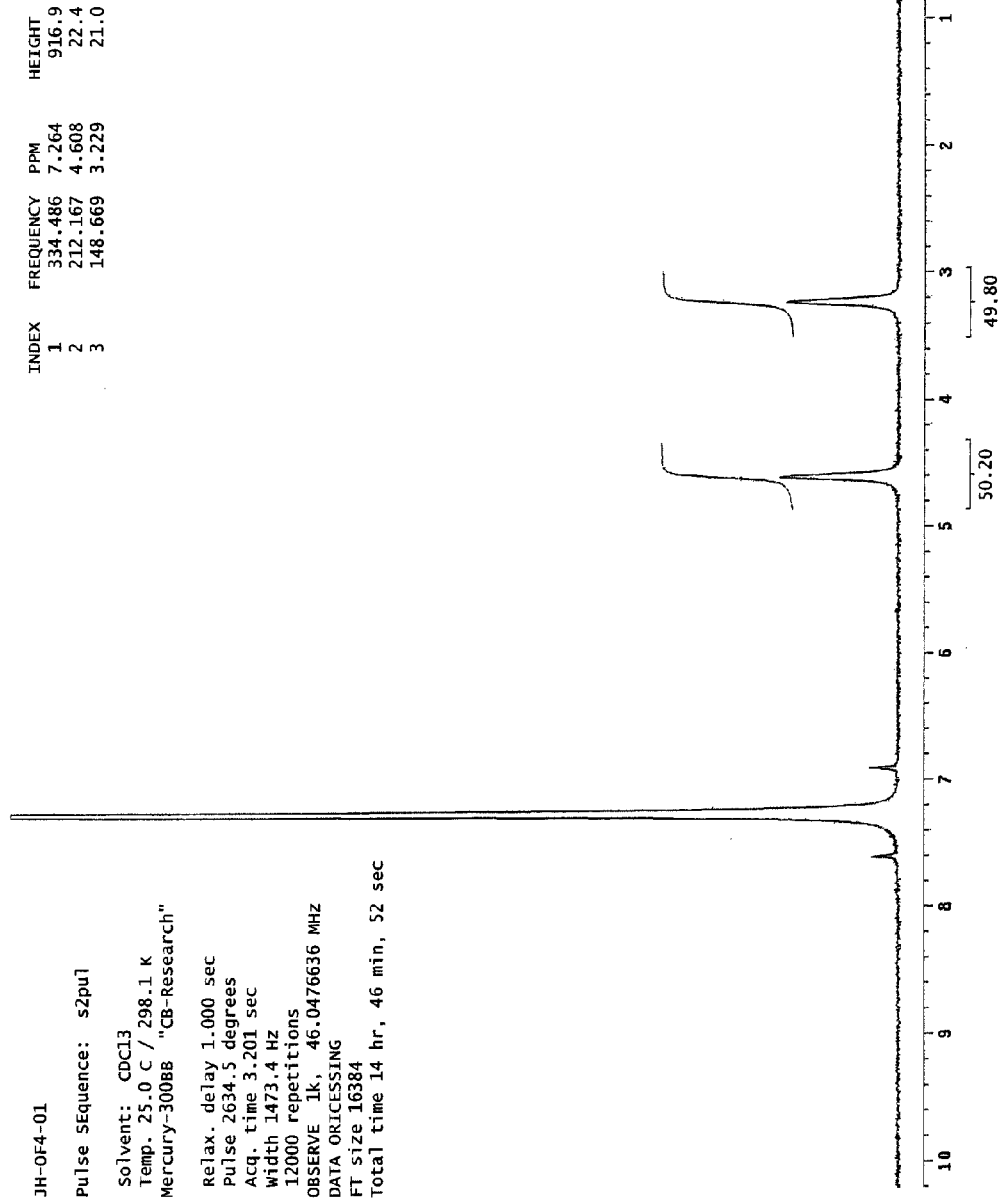
FIG. 3 provides a $^2$H NMR spectrum used in analysis of exemplary compound 14 as described in Example 5 below.

Compound 14 characterization: Purity: >99% by GC analysis on HP-5MS GC capillary column (30 m×250 μm×0.25 μm; hold at 50° C. for 1 min, ramp 20° C./min to 280° C., 1 min hold at 280° C.; mobile phase, 5% phenyl methyl siloxane, retention time=7.43 min). GC-MS, m/z=178.1 [M]$^+$. $^1$H NMR, COSY NMR, $^{13}$C NMR, $^{19}$F NMR, and $^2$H NMR spectra, where each was performed in CDCl$_3$, were consistent with product being compound 14. FIG. 3 provides a representative $^2$H NMR spectrum.

Example 6: Evaluation of Metabolic Stability in Human Liver Microsomes

Published accounts have observed that deuterium substitution can have variable and unpredictable effects on the rate of metabolism of a compound. See, e.g., Blake et al., 1975, *J. Pharm. Sci.* 64:367-391; Foster, 1985, *Adv. Drug Res.* 14:1-40; Kushner et al., 1999, *Can. J. Physiol. Pharmacol.* 79-88; Fisher et al., 2006, *Curr. Opin. Drug Discov. Devel.* 9:101-109; Fukuto et al., 1991, *J. Med. Chem.* 34:2871-2876.

This example demonstrates that metabolic half-lives of deuterated PTZ isotopologues differ from each other and from that of PTZ.

Human liver microsomes (Lot# FJM) were obtained from Celsis (Baltimore, Md.). Components of the NADPH regenerating system solution A (Lot#29850) and B (Lot#28594) were obtained from BD Gentest (Woburn, Mass.). Testosterone (Lot# FE111011-01) was purchased from Cerilliant (Round Rock, Tex.). All solvents and buffers were obtained from commercial sources and used without further purification.

Individual test compounds and testosterone were prepared as a 10 mM stock solution in DMSO. A mixture containing 50 mM potassium phosphate buffer pH 7.4, 3 mM MgCl$_2$, 1 mg/mL human liver microsomes and 1 μM test compound or testosterone was pre-incubated for 5 min at 37° C. in a shaking water bath. NADPH regenerating system (1.3 mM NADP$^+$, 3.3 mM glucose-6-phosphate, 0.4 U/mL glucose-6-phosphate dehydrogenase, and 3.3 mM magnesium chloride) were prepared by mixing 5 volume of solution A and 1 volume of solution B and pre-warmed at 37° C. in a shaking water bath. Reactions were initiated by adding NADPH regenerating system to the incubation mixtures. After 0, 5, 10, 15, 30 and 45 min of incubation, 0.1 mL reaction mixtures were removed from the incubation plate and mixed with 0.15 mL of ice-cold acetonitrile in an appropriate well of a 96-well crash plate. The 96-well crash plate was placed on ice for 15 min, and samples were centrifuged (2,500 g, 10 min, 4° C.) to precipitate protein. The supernatants were diluted 1:1 (v/v) with water containing 0.015 μM verapamil (internal standard) in 96-well shallow injection plate, which was sealed and submitted for LC/MS or LC/MS/MS analysis utilitzing a API 150 single quadrupole mas spectrometer.

The residual compound remaining (% R) was determined from LC/MS peak areas by comparison to a zero time point. Metabolic half-life ($t_{1/2}$) and intrinsic clearance (CLint) values were calculated from the slope of ln(%) plotted vs. time.

As shown in Table 1, under the assay conditions tested, the in vitro $t_{1/2}$ for Compounds 1, 2, and 4 was increased compared to the $t_{1/2}$ of PTZ.

TABLE 1

| Metabolic Stability of PTZ Derivatives in Presence of Human Liver Microsomes | | | |
|---|---|---|---|
| Compound | $t_{1/2}$ (min) | CLint (uL/min/mg) | $t_{1/2}$ increase over $t_{1/2}$ of PTZ (%) |
| PTZ | 521 | 1.3 | — |
| Compound 1 | 756 | 0.9 | 45.1 |
| Compound 2 | 554 | 1.3 | 6.3 |
| Compound 4 | 567 | 1.2 | 8.8 |
| Compound 3 | 506 | 1.4 | -2.9 |
| testosterone | 9.1 | 76 | n/a |

The results in Table 1 demonstrate that half-lives of deuterium PTZ isotopologues are not uniform and differ from each other and from PTZ depending upon the positions of the deuterium atoms within the molecule.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain embodiments, and are not intended to limit the scope of the disclosure. It will be apparent to those of ordinary skill in the art that various modifications and equivalents can be made without departing from the spirit and scope of the invention.

The examples set forth above are provided to give those of ordinary skill in the art with a complete disclosure and description of how to make and use the embodiments, and are not intended to limit the scope of the disclosure. Modifications of the above-described modes for carrying out the disclosure that are obvious to persons of skill in the art are intended to be within the scope of the following claims.

All publications, patents, and patent applications cited in this specification are incorporated herein by reference as if each such publication, patent, or patent application were specifically and individually indicated to be incorporated herein by reference.

What is claimed:

1. A compound, or a pharmaceutically acceptable salt thereof, wherein the compound is selected from the group consisting of

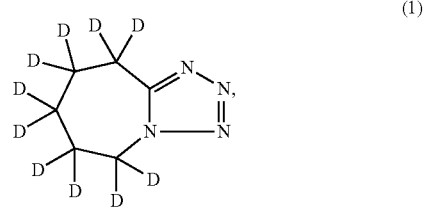

(1)

-continued

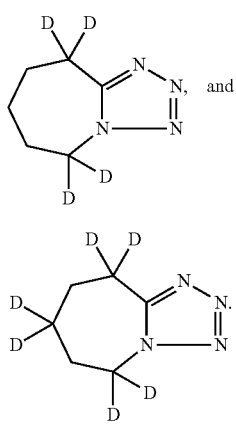

(2)

(4)

2. A pharmaceutical composition comprising the compound of claim 1, or a pharmaceutically acceptable salt thereof, and a pharmaceutically acceptable excipient.

3. A unit dose form comprising 0.1 mg to 1 g of the compound of claim 1, or a pharmaceutically acceptable salt thereof, and one or more pharmaceutically acceptable excipients.

4. A method of increasing blood flow, heart rate or breathing rate in an individual, comprising administering to the individual in need thereof an effective amount of the compound of claim 1, or a pharmaceutically acceptable salt thereof.

5. A method of suppressing cough in an individual, comprising administering to the individual in need thereof an effective amount of the compound of claim 1, or a pharmaceutically acceptable salt thereof.

6. A method for modulating gamma-aminobutyric acid receptor activity in an individual, comprising administering to the individual in need thereof an effective amount of the compound of claim 1, or a pharmaceutically acceptable salt thereof.

7. A method for improving cognitive function in an individual with Down syndrome, phenylketonuria, neurofibromatosis type 1, maple syrup urine disease, Rett syndrome, fetal alcohol syndrome, an autism spectrum disorder, circadian rhythm disruption, Alzheimer's disease, or dementia, comprising administering to the individual in need thereof an effective amount of the compound of claim 1, or a pharmaceutically acceptable salt thereof.

* * * * *